US007662948B2

(12) United States Patent
Kurreck et al.

(10) Patent No.: US 7,662,948 B2
(45) Date of Patent: Feb. 16, 2010

(54) ANTISENSE OLIGONUCLEOTIDES AGAINST VR1

(75) Inventors: Jens Kurreck, Berlin (DE); Volker A. Erdmann, Berlin (DE)

(73) Assignee: Gruenenthal GmbH, Aachen (DE)

( * ) Notice: Subject to any disclaimer, the term of this patent is extended or adjusted under 35 U.S.C. 154(b) by 807 days.

(21) Appl. No.: 10/376,341

(22) Filed: Mar. 3, 2003

(65) Prior Publication Data

US 2004/0002473 A1    Jan. 1, 2004

Related U.S. Application Data

(63) Continuation of application No. PCT/EP01/10081, filed on Aug. 31, 2001.

(30) Foreign Application Priority Data

Sep. 2, 2000  (DE) ............... 100 43 674
Sep. 4, 2000  (DE) ............... 100 43 702

(51) Int. Cl.
   *C07H 21/04* (2006.01)
(52) U.S. Cl. .................. 536/24.5
(58) Field of Classification Search ........ 536/23.1, 536/24.5; 514/44
   See application file for complete search history.

(56) References Cited

U.S. PATENT DOCUMENTS

| 5,744,308 | A  | * | 4/1998  | Guillou-Bonnici et al. ..... 435/6 |
| 6,278,038 | B1 | * | 8/2001  | Cone et al. .............. 800/3 |
| 6,335,180 | B1 | * | 1/2002  | Julius et al. ............ 435/69.1 |
| 6,482,611 | B1 | * | 11/2002 | Cortright et al. ......... 435/69.1 |
| 6,566,127 | B1 | * | 5/2003  | Pavco et al. ............ 435/325 |

FOREIGN PATENT DOCUMENTS

| EP | 0 943 683 | 9/1999 |
| GB | 2 346 882 | 8/2000 |
| WO | WO 9846272 A1 * | 10/1998 |
| WO | WO 99/09140 | 2/1999 |
| WO | WO 99/37675 | 7/1999 |
| WO | WO 00/22121 | 4/2000 |
| WO | WO 00/29577 | 5/2000 |
| WO | WO 00/32766 | 6/2000 |
| WO | WO 00/63415 | 10/2000 |
| WO | WO 03018631 A2 * | 3/2003 |

OTHER PUBLICATIONS

Soares et al. Construction and characterization of a normalized cDNA library Sep. 1995, Proc. Natl. Acad. Sci. vol. 91, pp. 9228-9232.*
Gomez-Navarro et al. Gene therapy for cancer 1999, European Journal of Cancer vol. 35(6): pp. 867-885.*
Agrawal et al. Antisense therapeutics: is it as simple as complementary base recognition? 2000 Mol. Med. Today: Reviews. vol. 61, pp. 72-81.*
Opalinska et al. Nucleic acid therapeutics: basic principlese and recent applications. 2002 Nature Reviews: Drug Discovery vol. 1, pp. 503-514.*
Jen et al. Suppression of gene expression by targeted disruption of messenger RNA: available options and current strategies 2000 Stem Cells vol. 18, pp. 307-319.*
Crooke, S. Progress in antisense technology 2004 Annu. Rev. Med. vol. 55, pp. 61-95.*
Santoro et al. A general purpose RNA cleaving DNA-enzyme 1997 Proc. Nat.. Acad. Sci. vol. 94: pp. 4262-4266 (see in particular figure 2).*
Simoncsits et al. Synthesis of pppGpN type dinucleotide derivatives: the 5' end sequence of some RNAs. 1975 Nuc. Acids. Res. vol. 2, No. 2, pp. 257-263.*
Sakai, Y. et al. Journal of Fermentation and Bioengineering, 1998; vol. 85(2), pp. 138-143.*
Kurreck et al. "Comparative Study of DNA Enzymes and Ribozymes against the Same full-length Messenger RNA of the Vanilloid Receptor Subtype I" *The Journal of Biological Chemistry*, vol. 277, No. 9, (2002) pp. 7099-7107. XP-001068907.
Caterina et al. "The capsaicin receptor: a heat-activated ion channel in the pain pathway" *Nature*, vol. 389, pp. 816-824 (1997). XP002942960.
Goila et al. "Sequence specific cleavage of the HIV-1 coreceptor CCR5 gene by a hammer-head ribozyme and a DNA-enzyme: inhibition of the coreceptor function by DNA-enzyme" *FEBS Letters* 436 1998) pp. 233-238.

* cited by examiner

*Primary Examiner*—J. E Angell
(74) *Attorney, Agent, or Firm*—Crowell & Moring LLP

(57) ABSTRACT

Antisense oligodeoxynucleotides against VR1, corresponding nucleotide constructs, cells containing said nucleotide constructs, pharmaceutical and diagnostic substances, uses thereof in pain therapy, and methods for diagnosing symptoms related to VR1 and for identifying pain-modulating substances.

32 Claims, 27 Drawing Sheets

Fig. 1)

| | | | | |
|---|---|---|---|---|
| (a) | 5'– | CATGACGGT | – 3' | (SEQ ID:1) |
| (b) | 5'– | GTCATGACGGTTAGG | – 3' | (SEQ ID:2) |
| (c) | 5'– | TGTCATGACGGTTAG | – 3' | (SEQ ID:3) |
| (d) | 5'– | ATGTCATGACGGTTA | – 3' | (SEQ ID:4) |
| (e) | 5'– | CATGTCATGACGGTT | – 3' | (SEQ ID:5) |
| (f) | 5'– | TGTCATGACGGTTAGG | – 3' | (SEQ ID:6) |
| (g) | 5'– | ATGTCATGACGGTTAG | – 3' | (SEQ ID:7) |
| (h) | 5'– | CATGTCATGACGGTTA | – 3' | (SEQ ID:8) |
| (i) | 5'– | ATGTCATGACGGTTAGG | – 3' | (SEQ ID:9) |
| (j) | 5'– | CATGTCATGACGGTTAG | – 3' | (SEQ ID:10) |
| (k) | 5'– | CATGTCATGACGGTTAGG | – 3' | (SEQ ID:11) |
| (l) | 5'– | GTCATGA GGTTAGG | – 3' | (SEQ ID:12) |
| | | Fragment I  Fragment III | | |
| (m) | 5'– | TGTCATGA GGTTAGGG | – 3' | (SEQ ID:13) |
| | | Fragment I  Fragment III | | |
| (n) | 5'– | ATGTCATGA GGTTAGGGG | – 3' | (SEQ ID:14) |
| | | Fragment I  Fragment III | | |
| (o) | 5'– | AUGUCAU ACGGUUA | – 3' | (SEQ ID:15) |
| | | Helix I  Helix III | | |
| (p) | 5'– | CAUGUCAU ACGGUUAG | – 3' | (SEQ ID:16) |
| | | Helix I  Helix III | | |
| (q) | 5'– | GCAUGUCAU ACGGUUAGG | – 3' | (SEQ ID:17) |
| | | Helix I  Helix III | | |

Fig. 2)

(a) 5'- CGTGGCGAT -3' (SEQ ID:18)

(b) 5'- GTCGTGGCGATTAGG -3' (SEQ ID:19)
(c) 5'- TGTCGTGGCGATTAG -3' (SEQ ID:20)
(d) 5'- ATGTCGTGGCGATTA -3' (SEQ ID:21)
(e) 5'- CATGTCGTGGCGATT -3' (SEQ ID:22)
(f) 5'- TGTCGTGGCGATTAGG -3' (SEQ ID:23)
(g) 5'- ATGTCGTGGCGATTAG -3' (SEQ ID:24)
(h) 5'- CATGTCGTGGCGATTA -3' (SEQ ID:25)
(i) 5'- ATGTCGTGGCGATTAGG -3' (SEQ ID:26)
(j) 5'- CATGTCGTGGCGATTAG -3' (SEQ ID:27)

(k) 5'- CATGTCGTGGCGATTAGG -3' (SEQ ID:28)

Fig. 3)

| | | | | |
|---|---|---|---|---|
| (a) | 5'- | GTTGACGGT | -3' | (SEQ ID:29) |
| (b) | 5'- | TTGTTGACGGTCTCA | -3' | (SEQ ID:30) |
| (c) | 5'- | CTTGTTGACGGTCTC | -3' | (SEQ ID:31) |
| (d) | 5'- | TCTTGTTGACGGTCT | -3' | (SEQ ID:32) |
| (e) | 5'- | ATCTTGTTGACGGTC | -3' | (SEQ ID:33) |
| (f) | 5'- | CTTGTTGACGGTCTCA | -3' | (SEQ ID:34) |
| (g) | 5'- | TCTTGTTGACGGTCTC | -3' | (SEQ ID:35) |
| (h) | 5'- | ATCTTGTTGACGGTCT | -3' | (SEQ ID:36) |
| (i) | 5'- | TCTTGTTGACGGTCTCA | -3' | (SEQ ID:37) |
| (j) | 5'- | ATCTTGTTGACGGTCTC | -3' | (SEQ ID:38) |
| (k) | 5'- | ATCTTGTTGACGGTCTCA | -3' | (SEQ ID:39) |

(l) 5'- TTGTTGA GGTCTCA -3'  (SEQ ID:40)
         Fragment I  Fragment III (m) 5'- CTTGTTGA GGTCTCAC -3'  (SEQ ID:41)
         Fragment I  Fragment III (n) 5'- TCTTGTTGA GGTCTCACC -3'  (SEQ ID:42)
         Fragment I  Fragment III (o) 5'- UCUUGUU ACGGUCU -3'  (SEQ ID:43)
         Helix I  Helix III (p) 5'- AUCUUGUU ACGGUCUC -3'  (SEQ ID:44)
         Helix I  Helix III (q) 5'- AAUCUUGUU ACGGUCUCA -3'  (SEQ ID:45)
         Helix I  Helix III

Fig. 4)

| | | | | |
|---|---|---|---|---|
| (a) | 5´- | GTTGACAGT | - 3´ | (SEQ ID:46) |
| (b) | 5´- | TTGTTGACAGTCTCA | - 3´ | (SEQ ID:47) |
| (c) | 5´- | CTTGTTGACAGTCTC | - 3´ | (SEQ ID:48) |
| (d) | 5´- | TCTTGTTGACAGTCT | - 3´ | (SEQ ID:49) |
| (e) | 5´- | ATCTTGTTGACAGTC | - 3´ | (SEQ ID:50) |
| (f) | 5´- | CTTGTTGACAGTCTCA | - 3´ | (SEQ ID:51) |
| (g) | 5´- | TCTTGTTGACAGTCTC | - 3´ | ((SEQ ID:52) |
| (h) | 5´- | ATCTTGTTGACAGTCT | - 3´ | (SEQ ID:53) |
| (i) | 5´- | TCTTGTTGACAGTCTCA | - 3´ | (SEQ ID:54) |
| (j) | 5´- | ATCTTGTTGACAGTCTC | - 3´ | (SEQ ID:55) |
| (k) | 5´- | ATCTTGTTGACAGTCTCA | - 3´ | (SEQ ID:56) |

(l) 5´-   TTGTTGA  AGTCTCA   - 3´   (SEQ ID:57)
           ⎵⎵⎵⎵⎵⎵⎵ ⎵⎵⎵⎵⎵⎵⎵
           Fragment I  Fragment III (m) 5´-   CTTGTTGA  AGTCTCAX   - 3´   (SEQ ID:58)
           ⎵⎵⎵⎵⎵⎵⎵⎵ ⎵⎵⎵⎵⎵⎵⎵⎵
           Fragment I  Fragment III (n) 5´-   TCTTGTTGA  AGTCTCAXX   - 3´   (SEQ ID:59)
           ⎵⎵⎵⎵⎵⎵⎵⎵⎵ ⎵⎵⎵⎵⎵⎵⎵⎵⎵
           Fragment I  Fragment III (o) 5´-   UCUUGUU  ACAGUCU   - 3´   (SEQ ID:60)
           ⎵⎵⎵⎵⎵⎵⎵ ⎵⎵⎵⎵⎵⎵⎵
           Helix I  Helix III (p) 5´-   AUCUUGUU  ACAGUCUC   - 3´   (SEQ ID:61)
           ⎵⎵⎵⎵⎵⎵⎵⎵ ⎵⎵⎵⎵⎵⎵⎵⎵
           Helix I  Helix III (q) 5´-   XAUCUUGUU  ACAGUCUCA   - 3´   (SEQ ID:62)
           ⎵⎵⎵⎵⎵⎵⎵⎵⎵ ⎵⎵⎵⎵⎵⎵⎵⎵⎵
           Helix I  Helix III

Fig. 5)

| | | | | |
|---|---|---|---|---|
| (a) | 5'- | CCTGACCTC | -3' | (SEQ ID:63) |
| (b) | 5'- | GGCCTGACCTCAGGG | -3' | (SEQ ID:64) |
| (c) | 5'- | CGGCCTGACCTCAGG | -3' | (SEQ ID:65) |
| (d) | 5'- | TCGGCCTGACCTCAG | -3' | (SEQ ID:66) |
| (e) | 5'- | CTCGGCCTGACCTCA | -3' | (SEQ ID:67) |
| (f) | 5'- | CGGCCTGACCTCAGGG | -3' | (SEQ ID:68) |
| (g) | 5'- | TCGGCCTGACCTCAGG | -3' | (SEQ ID:69) |
| (h) | 5'- | CTCGGCCTGACCTCAG | -3' | (SEQ ID:70) |
| (i) | 5'- | TCGGCCTGACCTCAGGG | -3' | (SEQ ID:71) |
| (j) | 5'- | CTCGGCCTGACCTCAGG | -3' | (SEQ ID:72) |
| (k) | 5'- | CTCGGCCTGACCTCAGGG | -3' | (SEQ ID:73) |
| (l) | 5'- | GGCCTGA CTCAGGG (Fragment I / Fragment III) | -3' | (SEQ ID:74) |
| (m) | 5'- | CGGCCTGA CTCAGGA (Fragment I / Fragment III) | -3' | (SEQ ID:75) |
| (n) | 5'- | TCGGCCTGA CTCAGGAG (Fragment I / Fragment III) | -3' | (SEQ ID:76) |
| (o) | 5'- | UCGGCCU ACCUCAG (Helix I / Helix III) | -3' | (SEQ ID:77) |
| (p) | 5'- | CUCGGCCU ACCUCAGG (Helix I / Helix III) | -3' | (SEQ ID:78) |
| (q) | 5'- | XCUCGGCCU ACCUCAGGG (Helix I / Helix III) | -3' | (SEQ ID:79) |

Fig. 6)

(a) 5'- CTTGACCGC -3' (SEQ ID:80)

(b) 5'- TGCTTGACCGCAGGG -3' (SEQ ID:81)
(c) 5'- CTGCTTGACCGCAGG -3' (SEQ ID:82)
(d) 5'- TCTGCTTGACCGCAG -3' (SEQ ID:83)
(e) 5'- CTCTGCTTGACCGCA -3' (SEQ ID:84)
(f) 5'- CTGCTTGACCGCAGGG -3' (SEQ ID:85)
(g) 5'- TCTGCTTGACCGCAGG -3' (SEQ ID:86)
(h) 5'- CTCTGCTTGACCGCAG -3' (SEQ ID:87)
(i) 5'- TCTGCTTGACCGCAGGG -3' (SEQ ID:88)
(j) 5'- CTCTGCTTGACCGCAGG -3' (SEQ ID:89)

(k) 5'- CTCTGCTTGACCGCAGGG -3' (SEQ ID:90)

(l) 5'- TGCTTGA CGCAGGG -3' (SEQ ID:91)
        Fragment I  Fragment III (m) 5'- CTGCTTGA CGCAGGGX -3' (SEQ ID:92)
        Fragment I  Fragment III (n) 5'- TCTGCTTGA CGCAGGGXX -3' (SEQ ID:93)
        Fragment I  Fragment III (o) 5'- UCUGCUU ACCGCAG -3' (SEQ ID:94)
        Helix I  Helix III (p) 5'- CUCUGCUU ACCGCAGG -3' (SEQ ID:95)
        Helix I  Helix III (q) 5'- XCUCUGCUU ACCGCAGGG -3' (SEQ ID:96)
        Helix I  Helix III

Fig. 7)

| | | | | |
|---|---|---|---|---|
| (a) | 5'- | GTGGACTCC | - 3' | (SEQ ID:97) |
| (b) | 5'- | GTGTGGACTCCATAG | - 3' | (SEQ ID:98) |
| (c) | 5'- | GGTGTGGACTCCATA | - 3' | (SEQ ID:99) |
| (d) | 5'- | TGGTGTGGACTCCAT | - 3' | (SEQ ID:100) |
| (e) | 5'- | GTGGTGTGGACTCCA | - 3' | (SEQ ID:101) |
| (f) | 5'- | GGTGTGGACTCCATAG | - 3' | (SEQ ID:102) |
| (g) | 5'- | TGGTGTGGACTCCATA | - 3' | (SEQ ID:103) |
| (h) | 5'- | GTGGTGTGGACTCCAT | - 3' | (SEQ ID:104) |
| (i) | 5'- | TGGTGTGGACTCCATAG | - 3' | (SEQ ID:105) |
| (j) | 5'- | GTGGTGTGGACTCCATA | - 3' | (SEQ ID:106) |
| (k) | 5'- | GTGGTGTGGACTCCATAG | - 3' | (SEQ ID:107) |
| (l) | 5'- | GTGTGGA TCCATAG | - 3' | (SEQ ID:108) |
| | | Fragment I  Fragment III | | |
| (m) | 5'- | GGTGTGGA TCCATAGG | - 3' | (SEQ ID:109) |
| | | Fragment I  Fragment III | | |
| (n) | 5'- | TGGTGTGGA TCCATAGGC | - 3' | (SEQ ID:110) |
| | | Fragment I  Fragment III | | |
| (o) | 5'- | UGGUGUG ACUCCAU | - 3' | (SEQ ID:111) |
| | | Helix I  Helix III | | |
| (p) | 5'- | GUGGUGUG ACUCCAUA | - 3' | (SEQ ID:112) |
| | | Helix I  Helix III | | |
| (q) | 5'- | XGUGGUGUG ACUCCAUAG | - 3' | (SEQ ID:113) |
| | | Helix I  Helix III | | |

Fig. 8)

| | | | | |
|---|---|---|---|---|
| (a) | 5'- | GTGGACTCA | -3' | (SEQ ID:114) |
| (b) | 5'- | ACGTGGACTCAGACG | -3' | (SEQ ID:115) |
| (c) | 5'- | GACGTGGACTCAGAC | -3' | (SEQ ID:116) |
| (d) | 5'- | CGACGTGGACTCAGA | -3' | (SEQ ID:117) |
| (e) | 5'- | GCGACGTGGACTCAG | -3' | (SEQ ID:118) |
| (f) | 5'- | GACGTGGACTCAGACG | -3' | (SEQ ID:119) |
| (g) | 5'- | CGACGTGGACTCAGAC | -3' | (SEQ ID:120) |
| (h) | 5'- | GCGACGTGGACTCAGA | -3' | (SEQ ID:121) |
| (i) | 5'- | CGACGTGGACTCAGACG | -3' | (SEQ ID:122) |
| (j) | 5'- | GCGACGTGGACTCAGAC | -3' | (SEQ ID:123) |
| (k) | 5'- | GCGACGTGGACTCAGACG | -3' | (SEQ ID:124) |
| (l) | 5'- | ACGTGGA TCAGACG | -3' | (SEQ ID:125) |
| | | Fragment I  Fragment III | | |
| (m) | 5'- | GACGTGGA TCAGACGX | -3' | (SEQ ID:126) |
| | | Fragment I  Fragment III | | |
| (n) | 5'- | CGACGTGGA TCAGACGXX | -3' | (SEQ ID:127) |
| | | Fragment I  Fragment III | | |
| (o) | 5'- | CGACGUG ACUCAGA | -3' | (SEQ ID:128) |
| | | Helix I  Helix III | | |
| (p) | 5'- | GCGACGUG ACUCAGAC | -3' | (SEQ ID:129) |
| | | Helix I  Helix III | | |
| (q) | 5'- | XGCGACGUG ACUCAGACG | -3' | (SEQ ID:130) |
| | | Helix I  Helix III | | |

Fig. 9)

| | | | | |
|---|---|---|---|---|
| (a) | 5´- | GGGGACTCA | - 3´ | (SEQ ID:131) |
| (b) | 5´- | GTGGGGACTCAGACT | - 3´ | (SEQ ID:132) |
| (c) | 5´- | GGTGGGGACTCAGAC | - 3´ | (SEQ ID:133) |
| (d) | 5´- | GGGTGGGGACTCAGA | - 3´ | (SEQ ID:134) |
| (e) | 5´- | GGGGTGGGGACTCAG | - 3´ | (SEQ ID:135) |
| (f) | 5´- | GGTGGGGACTCAGACT | - 3´ | (SEQ ID:136) |
| (g) | 5´- | GGGTGGGGACTCAGAC | - 3´ | (SEQ ID:137) |
| (h) | 5´- | GGGGTGGGGACTCAGA | - 3´ | (SEQ ID:138) |
| (i) | 5´- | GGGTGGGGACTCAGACT | - 3´ | (SEQ ID:139) |
| (j) | 5´- | GGGGTGGGGACTCAGAC | - 3´ | (SEQ ID:140) |
| (k) | 5´- | GGGGTGGGGACTCAGACT | - 3´ | (SEQ ID:141 |

(l) 5´- GTGGGGA TCAGACT - 3´ (SEQ ID:142)
       Fragment I   Fragment III (m) 5´- GGTGGGGA TCAGACTC - 3´ (SEQ ID:143)
       Fragment I   Fragment III (n) 5´- GGGTGGGGA TCAGACTCC - 3´ (SEQ ID:144)
       Fragment I   Fragment III (o) 5´- GGGUGGG ACUCAGA - 3´ (SEQ ID:145)
       Helix I   Helix III (p) 5´- GGGGUGGG ACUCAGAC - 3´ (SEQ ID:146)
       Helix I   Helix III (q) 5´- XGGGGUGGG ACUCAGACU - 3´ (SEQ ID:147)
       Helix I   Helix III

Fig. 10)

(a)  5'-   GGGTCCGCA         -3'   (SEQ ID:148)

(b)  5'-   GTGGGTCCGCAGCAG    -3'   (SEQ ID:149)
(c)  5'-   AGTGGGTCCGCAGCA    -3'   (SEQ ID:150)
(d)  5'-   GAGTGGGTCCGCAGC    -3'   (SEQ ID:151)
(e)  5'-   GGAGTGGGTCCGCAG    -3'   (SEQ ID:152)
(f)  5'-   AGTGGGTCCGCAGCAG   -3'   (SEQ ID:153)
(g)  5'-   GAGTGGGTCCGCAGCA   -3'   (SEQ ID:154)
(h)  5'-   GGAGTGGGTCCGCAGC   -3'   (SEQ ID:155)
(i)  5'-   GAGTGGGTCCGCAGCAG  -3'   (SEQ ID:156)
(j)  5'-   GGAGTGGGTCCGCAGCA  -3'   (SEQ ID:157)

(k)  5'-   GGAGTGGGTCCGCAGCAG -3'   (SEQ ID:158)

Fig. 11)

| | | | | |
|---|---|---|---|---|
| (a) | 5´- | CTTGACAAA | - 3´ | (SEQ ID:159) |
| (b) | 5´- | CGCTTGACAAATCTG | - 3´ | (SEQ ID:160) |
| (c) | 5´- | GCGCTTGACAAATCT | - 3´ | (SEQ ID:161) |
| (d) | 5´- | TGCGCTTGACAAATC | - 3´ | (SEQ ID:162) |
| (e) | 5´- | ATGCGCTTGACAAAT | - 3´ | (SEQ ID:163) |
| (f) | 5´- | GCGCTTGACAAATCTG | - 3´ | (SEQ ID:164) |
| (g) | 5´- | TGCGCTTGACAAATCT | - 3´ | (SEQ ID:165) |
| (h) | 5´- | ATGCGCTTGACAAATC | - 3´ | (SEQ ID:166) |
| (i) | 5´- | TGCGCTTGACAAATCTG | - 3´ | (SEQ ID:167) |
| (j) | 5´- | ATGCGCTTGACAAATCT | - 3´ | (SEQ ID:168) |
| (k) | 5´- | ATGCGCTTGACAAATCTG | - 3´ | (SEQ ID:169) |
| (l) | 5´- | CGCTTGA  AAATCTG | - 3´ | (SEQ ID:170) |
| | | Fragment I  Fragment III | | |
| (m) | 5´- | GCGCTTGA  AAATCTGT | - 3´ | (SEQ ID:172) |
| | | Fragment I  Fragment III | | |
| (n) | 5´- | TGCGCTTGA  AAATCTGTC | - 3´ | (SEQ ID:173) |
| | | Fragment I  Fragment III | | |
| (o) | 5´- | UGCGCUU  ACAAAUC | - 3´ | (SEQ ID:174) |
| | | Helix I  Helix III | | |
| (p) | 5´- | AUGCGCUU  ACAAAUCU | - 3´ | (SEQ ID:175) |
| | | Helix I  Helix III | | |
| (q) | 5´- | GAUGCGCUU  ACAAAUCUG | - 3´ | (SEQ ID:176) |
| | | Helix I  Helix III | | |

Fig. 12)

(a) 5'- CTTGACGAA -3' (SEQ ID:177)

(b) 5'- CGCTTGACGAATCTG -3' (SEQ ID:178)
(c) 5'- GCGCTTGACGAATCT -3' (SEQ ID:179)
(d) 5'- TGCGCTTGACGAATC -3' (SEQ ID:180)
(e) 5'- ATGCGCTTGACGAAT -3' (SEQ ID:181)
(f) 5'- GCGCTTGACGAATCTG -3' (SEQ ID:182)
(g) 5'- TGCGCTTGACGAATCT -3' (SEQ ID:183)
(h) 5'- ATGCGCTTGACGAATC -3' (SEQ ID:184)
(i) 5'- TGCGCTTGACGAATCTG -3' (SEQ ID:185)
(j) 5'- ATGCGCTTGACGAATCT -3' (SEQ ID:186)

(k) 5'- ATGCGCTTGACGAATCTG -3' (SEQ ID:187)

(l) 5'- CGCTTGA GAATCTG -3' (SEQ ID:188)
      Fragment I  Fragment III
(m) 5'- GCGCTTGA GAATCTGX -3' (SEQ ID:189)
      Fragment I  Fragment III
(n) 5'- TGCGCTTGA GAATCTGXX -3' (SEQ ID:190)
      Fragment I  Fragment III (o) 5'- UGCGCUU ACGAAUC -3' (SEQ ID:191)
      Helix I   Helix III
(p) 5'- AUGCGCUU ACGAAUCU -3' (SEQ ID:192)
      Helix I   Helix III
(q) 5'- XAUGCGCUU ACGAAUCUG -3' (SEQ ID:193)
      Helix I   Helix III

Fig. 13)

| | | | | |
|---|---|---|---|---|
| (a) | 5'- | CCAGACATG | - 3' | (SEQ ID:194) |
| (b) | 5'- | CTCCAGACATGTGGA | - 3' | (SEQ ID:195) |
| (c) | 5'- | GCTCCAGACATGTGG | - 3' | (SEQ ID:196) |
| (d) | 5'- | AGCTCCAGACATGTG | - 3' | (SEQ ID:197) |
| (e) | 5'- | CAGCTCCAGACATGT | - 3' | (SEQ ID:198) |
| (f) | 5'- | GCTCCAGACATGTGGA | - 3' | (SEQ ID:199) |
| (g) | 5'- | AGCTCCAGACATGTGG | - 3' | (SEQ ID:200) |
| (h) | 5'- | CAGCTCCAGACATGTG | - 3' | (SEQ ID:201) |
| (i) | 5'- | AGCTCCAGACATGTGGA | - 3' | (SEQ ID:202) |
| (j) | 5'- | CAGCTCCAGACATGTGG | - 3' | (SEQ ID:203) |
| (k) | 5'- | CAGCTCCAGACATGTGGA | - 3' | (SEQ ID:204) |

(l) 5'- CTCCAGA ATGTGGA - 3' (SEQ ID:205)
      Fragment I  Fragment III (m) 5'- GCTCCAGA ATGTGGAA - 3' (SEQ ID:206)
      Fragment I  Fragment III (n) 5'- AGCTCCAGA ATGTGGAAT - 3' (SEQ ID:207)
      Fragment I  Fragment III (o) 5'- AGCUCCA ACAUGUG - 3' (SEQ ID:208)
      Helix I  Helix III (p) 5'- CAGCUCCA ACAUGUGG - 3' (SEQ ID:209)
      Helix I  Helix III (q) 5'- XCAGCUCCA ACAUGUGGA - 3' (SEQ ID:210)
      Helix I  Helix III

Fig. 14)

(a) 5'- CCAGGCAGG -3' (SEQ ID:211)

(b) 5'- CTCCAGGCAGGTGGA -3' (SEQ ID:212)
(c) 5'- GCTCCAGGCAGGTGG -3' (SEQ ID:213)
(d) 5'- AGCTCCAGGCAGGTG -3' (SEQ ID:214)
(e) 5'- CAGCTCCAGGCAGGT -3' (SEQ ID:215)
(f) 5'- GCTCCAGGCAGGTGGA -3' (SEQ ID:216)
(g) 5'- AGCTCCAGGCAGGTGG -3' (SEQ ID:217)
(h) 5'- CAGCTCCAGGCAGGTG -3' (SEQ ID:218)
(i) 5'- AGCTCCAGGCAGGTGGA -3' (SEQ ID:219)
(j) 5'- CAGCTCCAGGCAGGTGG -3' (SEQ ID:220)

(k) 5'- CAGCTCCAGGCAGGTGGA -3' (SEQ ID:221)

Fig. 15)

| | | | | |
|---|---|---|---|---|
| (a) | 5'- | TACGACTCC | -3' | (SEQ ID:222) |
| (b) | 5'- | GGTACGACTCCTGGT | -3' | (SEQ ID:223) |
| (c) | 5'- | GGGTACGACTCCTGG | -3' | (SEQ ID:224) |
| (d) | 5'- | CGGGTACGACTCCTG | -3' | (SEQ ID:225) |
| (e) | 5'- | CCGGGTACGACTCCT | -3' | (SEQ ID:226) |
| (f) | 5'- | GGGTACGACTCCTGGT | -3' | (SEQ ID:227) |
| (g) | 5'- | CGGGTACGACTCCTGG | -3' | (SEQ ID:228) |
| (h) | 5'- | CCGGGTACGACTCCTG | -3' | (SEQ ID:229) |
| (i) | 5'- | CGGGTACGACTCCTGGT | -3' | (SEQ ID:230) |
| (j) | 5'- | CCGGGTACGACTCCTGG | -3' | (SEQ ID:231) |
| (k) | 5'- | CCGGGTACGACTCCTGGT | -3' | (SEQ ID:232) |

(l) 5'- GGTACGA TCCTGGT -3' (SEQ ID:233)
       Fragment I   Fragment III (m) 5'- GGGTACGA TCCTGGTA -3' (SEQ ID:234)
        Fragment I   Fragment III (n) 5'- CGGGTACGA TCCTGGTAG -3' (SEQ ID:235)
         Fragment I    Fragment III (o) 5'- CGGGUAC ACUCCUG -3' (SEQ ID:236)
        Helix I  Helix III (p) 5'- CCGGGUAC ACUCCUGG -3' (SEQ ID:237)
         Helix I   Helix III (q) 5'- XCCGGGUAC ACUCCUGGU -3' (SEQ ID:238)
          Helix I    Helix III

Fig. 16)

(a) 5´-         TGCGGCTCT         -3´      (SEQ ID:239)

(b) 5´-       GGTGCGGCTCTTGGC     -3´      (SEQ ID:240)
(c) 5´-       GGGTGCGGCTCTTGG     -3´      (SEQ ID:241)
(d) 5´-       CGGGTGCGGCTCTTG     -3´      (SEQ ID:242)
(e) 5´-       CCGGGTGCGGCTCTT     -3´      (SEQ ID:243)
(f) 5´-       GGGTGCGGCTCTTGGC    -3´      (SEQ ID:244)
(g) 5´-       CGGGTGCGGCTCTTGG    -3´      (SEQ ID:245)
(h) 5´-       CCGGGTGCGGCTCTTG    -3´      (SEQ ID:246)
(i) 5´-       CGGGTGCGGCTCTTGGC   -3´      (SEQ ID:247)
(j) 5´-       CCGGGTGCGGCTCTTGG   -3´      (SEQ ID:248)

(k) 5´-       CCGGGTGCGGCTCTTGGC  -3´      (SEQ ID:249)

Hammerhead-Ribozyme

N: optional nucleotide

N': nucleotide complementary to N

X: A, C or U

Y: pyrimidine nucleotide

R: purine nucleotide complementary to Y

Modified according to:
Vaish, N. K. et al. (1998) Nucl. Acids Res. 26, 5237-5242

Hammerhead-Ribozyme V 16 (7/7)

N: optional nucleotide

N': nucleotide complementary to nucleotide of Helix I + III

X: A, C or U

Y: pyrimidine nucleotide

R: purine nucleotide complementary to Y

ANTISENSE OLIGONUCLEOTIDES AGAINST VR1

CROSS REFERENCE TO RELATED APPLICATIONS

The present application is a continuation of International Patent Application No. PCT/EP01/10081, filed Aug. 31, 2001, designating the United States of America and published in German as WO 02/18407 A2, the entire disclosure of which is incorporated herein by reference. Priority is claimed based on Federal Republic of Germany Patent Application Nos. 100 43 674.9, filed Sep. 2, 2000, and 100 43 702.8, filed Sep. 4, 2000

BACKGROUND AND SUMMARY OF THE INVENTION

The invention relates to antisense oligodeoxynucleotides against VR1, to corresponding nucleotide constructs, to cells, pharmaceutical preparations and diagnostic preparations containing these, to the use thereof in pain therapy and to methods for diagnosing symptoms associated with VR1 and for identifying pain-modulating substances.

The effective treatment of pain is a major challenge to molecular medicine. Acute and transient pain is an important bodily signal protecting people from severe injury by their environment or by overloading their body. In contrast, chronic pain, which lasts longer than the cause of the pain and the anticipated time frame for cure, has no known biological function and affects hundreds of millions of people worldwide. In the Federal Republic of Germany alone, some 7.5 million people suffer from chronic pain. Unfortunately, pharmacological treatment of chronic pain is still unsatisfactory and thus remains a challenge to current medical research. Currently existing analgesics often have an inadequate action and sometimes have severe side effects.

The search is thus now on for new targets or endogenous body structures which appear to provide a way of exerting pain-modulating action, for example using low molecular weight active substances or other compounds such as antisense oligodeoxynucleotides (ODN), in particular for the treatment of chronic pain.

The vanilloid receptor subtype 1 (VR1, also known as the capsaicin receptor) cloned by Caterina et al. (1997) is a promising starting point for the development of new analgesic drugs. This receptor is a cation channel which is predominantly expressed by primary sensory neurons (Catarina et al. 1997). VR1 is activated by capsaicin, a component of chillies, heat (>43° C.) and a low pH as a result of tissue injury, and brings about a calcium influx in primary afferents. VR1 knockout mice did not develop thermal hyperalgesia after tissue injury or inflammation (Caterina et al., 2000; Davis et al., 2000).

Antisense oligodeoxynucleotides, ribozymes and other catalytic nucleic acids may be used for the treatment, in particular of chronic pain, by degrading or modifying the mRNA of selected targets, in the case of the present invention the above-described VR1, to down-regulate the expression thereof and thus reduce the number of receptors per cell. The ODN attach themselves to the mRNA, so firstly blocking translation and secondly initiating degradation of the mRNA by RNase H, which cleaves the DNA/RNA duplex. Porreca et al. (1999) were able to demonstrate that intrathecally administered ODNs against the PN3/SNS channel in rats prevent the development of hyperalgesia and allodynia due to chronic nerve or tissue damage.

Even once the sequence of VR1 is known, effective blocking and cleavage of the mRNA in particular depends upon the selection of the correct antisense oligodeoxynucleotides, ribozymes and other catalytic nucleic acids. The target's mRNA is usually folded and only a few sites are accessible for attachment and subsequent cleavage. Nothing is known in the prior art about how to select the ODN correctly.

DESCRIPTION OF THE INVENTION

The object of the present document was accordingly to develop antisense oligodeoxynucleotides and catalytic nucleic acids together with corresponding ribozymes against the mRNA of the vanilloid receptor. The present invention accordingly provides an oligonucleotide containing or corresponding to a base sequence according to one of sequences (b) to (j) in each of FIG. 1, 2, 4, 5, 6, 7, 8, 9, 10, 11, 12, 13, 14, 15 or 16 or a sequence differing therefrom by at most one different base, wherein the base difference is not located in the sequence domain shown in sequence (a). For the purposes of the present invention, oligonucleotide means a molecule having between 2 and 40 nucleotides.

The present invention also provides an oligonucleotide containing or corresponding to a base sequence according to one of sequences (b) to (j) in one of FIG. 1, 2, 3, 4, 5, 6, 7, 8, 9, 10, 11, 12, 13, 14, 15 or 16.

The present invention also provides an oligonucleotide containing or corresponding to a base sequence according to (k) in one of FIG. 1, 2, 4, 5, 6, 7, 8, 9, 10, 11, 12, 13, 14, 15 or 16, or a sequence differing therefrom by at most two different bases, preferably one, wherein the base difference(s) is (are) not located in the sequence domain shown in (a).

The present invention also provides an oligonucleotide containing or corresponding to a base sequence according to (k) in each of FIG. 1, 2, 3, 4, 5, 6, 7, 8, 9, 10, 11, 12, 13, 14, 15 or 16.

The present invention preferably also provides an oligonucleotide which has a length of 15 to 30, preferably of 15 to 25, in particular 17 to 19, or exactly 18, nucleotides.

The present invention also preferably provides an oligonucleotide (hereinafter denoted oligonucleotide A) according to one of the above-stated oligonucleotide forms in which, optionally with one different base, the base sequence contained in the oligonucleotides or corresponding thereto may be found in one of FIG. 1, 2, 3, 4, 9, 10, 11, 12, 15 or 16. These in particular comprise oligonucleotides which have been found to be particularly effective or contain corresponding, optionally slightly different, sequences, which bind strongly to the mRNA of VR1 (see oligos V15, V30, V2, V16 and V4 or the corresponding human sequences).

The present invention also preferably provides an oligonucleotide (hereinafter denoted oligonucleotide B) in which, optionally with one different base, the base sequence contained in the oligonucleotides or corresponding thereto may be found in one of FIG. 1, 2, 3, 4, 11 or 12, preferably 1, 3 or 11, in particular 1 or 3.

The present invention preferably provides an oligonucleotide according to the invention which comprises at least one modified or unmodified ribose, at least one modified or unmodified phosphodiester bond and/or at least one modified or unmodified base.

The present invention preferably provides an oligonucleotide according to the invention, in which at least one of the nucleotides, in particular two or more of the nucleotides, are "locked nucleic acids" (LNAs) or at least one of the nucleotides, in particular all of the nucleotides, are phosphorothioates, preferably one in which two or more of the nucleotides are "locked nucleic acids (LNAs). "Locked nucleic acids" (LNAs) are ribonucleotides which contain a methylene bridge which joins the 2' oxygen of the ribose with the 4' carbon (see FIG. 27). Braasch D. A. and Corey, D. R. (2001), Locked nucleic acids (LNA); fine-tuning the recognition of DNA and RNA. Chem. Biol. 8, 1-7, provide an overview of LNAs. This article is herein explicitly incorporated by reference in its entirety. LNAs are available commercially, for example, from the company Proligo, Boulder, Colo., USA. Phosphorothioates are also known to the person skilled in the art and may be ordered, for example, from MWG-Biotech AG, Ebersberg, Germany.

Preferred oligonucleotides are those in which the LNAs are located at the 5' and 3' end of the oligonucleotide, preferably in each case the final 2-5 nucleotides, in particular in each case the final 3 or 4 nucleotides, on the 3' and 5' end of the oligonucleotide are LNAs. Prefereably, oligonucleotides of the invention have >6, in particular >8 contiguous nucleotides in the oligonucleotide that are not LNAs. Preferably, of the nucleotides shown in the sequence domain according to the particular, sequence (a) of the oligonucleotide according to one of FIGS. 1 to 16, at most one or none of the nucleotides is in each case an LNA.

In the case of oligonucleotides modified with LNAs or phosphorothioates, it is particularly preferred if the oligonucleotide is an oligonucleotide A according to the invention or an oligonucleotide B according to the invention, preferably an oligonucleotide B according to the invention (see above).

In general, the present invention specifically provides nucleic acids, in particular oligonucleotides, in which two or more of the nucleotides are "locked nucleic acids" (LNAs), in which the LNAs are on the 5' and 3' end of the oligonucleotide, preferably in each case the final 2-5 nucleotides, in particular in each case the final 3 or 4 nucleotides, on the 3' and 5' end of the oligonucleotide are LNAs, and/or in which >6, in particular >8 contiguous nucleotides in the oligonucleotide are not LNAs. The embodiments previously explained with regard to the LNAs also apply to this subject matter of the invention.

The present invention also preferably provides a polynucleotide construct containing at least one oligonucleotide according to the invention. Polynucleotide construct should here be taken to have a very wide meaning. It includes RNA and DNA and nucleotides from a length of at least 20 nucleotides. A "recombinant" polynucleotide construct should here be taken to be a general designation for any kind of DNA or RNA molecules which have been obtained by in vitro linkage of DNA or RNA molecules. Polynucleotide is taken to have the following meaning: the underlying nucleotide is a fundamental nucleic acid building block essentially consisting of nucleic base, pentose and phosphoric acid. This corresponds to a high molecular weight polynucleotide prepared from two or more nucleotides linked together by phosphoric acid/pentose esterification. However, the invention also includes modified polynucleotides which, while they retain the sequence of bases, have a modified backbone instead of phosphoric acid/pentose.

The present invention also preferably provides a polynucleotide construct containing in two separate domains, two nucleotide subsequences Fragment I and Fragment III according to one of sequences (l)-(n) or the two nucleotide subsequences helix I and helix III according to one of sequences (o)-(q) in one of FIG. 1, 3, 4, 5, 6, 7, 8, 9, 11, 12, 13 or 15, or nucleotide subsequences differing from these nucleotide subsequences in each case by at most one base. Further details relating to the division of the two domains may be found in FIG. 24 (helix I and helix III/ribozyme) and in Santoro et al. (1997) FIG. 2, p. 4264 (Fragment I and Fragment III/DNA enzyme), the entire content of the latter is herein explicitly incorporated by reference.

The present invention also preferably provides a polynucleotide construct which codes for at least one oligonucleotide according to the invention. This in particular comprises DNA to be read out or a vector containing DNA or RNA, the product of which is or may be an oligonucleotide according to the invention.

The present invention also particularly preferably provides a polynucleotide construct according to the invention which comprises a ribozyme, a DNA enzyme, a vector, in particular an expression vector, or a peptide nucleic acid (PNA).

The following definitions apply for the purposes of the present invention:

Cloning vector: A general name for nucleic acid molecules acting as vectors or carriers for foreign genes or parts thereof during cloning.

Expression vector: A name for specially constructed cloning vectors which, once inserted in a suitable host cell, permit the transcription and translation of the foreign gene cloned into the vector.

PNA: Standard international abbreviation for peptide nucleic acids. Peptide-linked amino acids here form a chain, the amino acids bearing as side chain a base capable of hybridisation with DNA or RNA.

Sequence: A succession of nucleotides or amino acids. For the purposes of the present invention, sequence is intended to mean nucleic acid sequence.

Ribozyme: A name for a catalytically active ribonucleic acid (for example ligase, endonuclease, polymerase, exonuclease), see for example hammerhead ribozyme according to FIG. 24 or 25 and the description of the Figures or see Vaish, N. K. et al. (1998), Nucl. Acid Res. 26, 5237-5242.

DNA enzyme: A name for a DNA molecule which exhibits catalytic activity (for example ligase, endonuclease, polymerase, exonuclease), see for example DNA enzyme 10-23 according to FIG. 26 and the description of the Figure, or see Santoro and Joyce (1997) Proc. Natl. Acad. Sci. USA 94, 4262-4266.

Catalytic RNA/DNA: A general name for ribozymes or DNA enzymes (see above).

The present invention also preferably provides a polynucleotide construct containing in two separate domains two nucleotide subsequences, as described above, wherein said construct comprises a ribozyme, preferably a "hammerhead" ribozyme, or a DNA enzyme, preferably a type 10-23 or 12-32 DNA enzyme. It is particularly preferred and selected if said construct comprises a DNA enzyme containing at least the nucleotide subsequences Fragment I and Fragment III according to one of sequences (l) to (n), preferably (n), in one of FIG. 1, 3, 4, 5, 6, 7, 8, 9, 11, 12 or 13; preferably 1, 3, 7 or 11, in particular 1 or 3; or preferably 4, 6, 8 or 12, in particular 4 or 12.

It is particularly preferred and selected if said polynucleotide construct comprises a ribozyme containing at least the nucleotide subsequences helix I and helix III according to one of sequences (o) to (q), preferably (o), in one of FIG. 1, 3, 4, 5, 6, 8, 11 or 12; preferably 1, 3 or 11, in particular 11; or preferably 4, 6, 8 or 12, in particular 4 or 12.

Specifically, a preferred embodiment may in particular be found in FIGS. 24 and 25. FIG. 24 is a general diagram of a "hammerhead" ribozyme after Vaish, N. K. et al. (1998), Nucl. Acid Res. 26, 5237-5242 with the "recognition arms" helix I and helix III, into which the helices I and III according to the invention according to sequences (o)-(q) in one of FIG.

1, 3, 4, 5, 6, 7, 8, 9, 11, 12, 13 or 15 are inserted, in order to obtain the hammerhead ribozymes according to the invention. The fragment helix I here replaces in each case in one of FIG. 1, 3, 4, 5, 6, 7, 8, 9, 11, 12, 13 or 15 the desired nucleotides in helix I according to FIG. 24 in such a manner that the first nucleotide on the 3' end of helix I in each case in one of FIG. 1, 3, 4, 5, 6, 7, 8, 9, 11, 12, 13 or 15 replaces the first desired nucleotide "N" on the 3' end of helix I of FIG. 24 and the following desired nucleotides "N" in helix I, FIG. 24 towards the 5' end are replaced by the nucleotides which are shown in one of sequences (o) to (q) of helix I in each case in one of FIG. 1, 3, 4, 5, 6, 7, 8, 9, 11, 12, 13 or 15. The nucleotides "A" and "C" on the 5' end of helix III in one of FIG. 1, 3, 4, 5, 6, 7, 8, 9, 11, 12, 13 or 15 in each case replace the nucleotides "A" and "C" in helix III in FIG. 24, and the following desired nucleotides "N" in helix III, FIG. 24 are replaced in the 5' end direction by the nucleotides which are shown in one of sequences (o)-(q), helix III, in each case in one of FIG. 1, 3, 4, 5, 6, 7, 8, 9, 11, 12, 13 or 15. FIG. 25 shows a specific example. The hammerhead ribozyme V16 (7/7) is derived from FIG. 24 and FIG. 11. The designation ribozyme V16 (7/7) here means that the enzyme is oriented towards the GUC site of oligo V16 and contains 7 nucleotides in each of the "recognition arms" (helix I and helix III), in this case according to helix I and helix III of sequence (o) in FIG. 1. The same applies to all ribozymes according to sequences (o to q) in each case in one of FIG. 1, 3, 4, 5, 6, 7, 8, 9, 11, 12, 13 or 15.

Specifically, a preferred embodiment may in particular be found in FIG. 26. FIG. 26 is a general diagram of a type "10-23" DNA enzyme according to Santoro et al., 1997, FIG. 2, p. 4264. The upper strand marked with an arrow is the RNA strand to be cleaved, the arrow showing the cleavage site, while the lower strand is a representation of the DNA enzyme. With regard to the present application, in the upper strand the "Y"="U" and the "R"="G", a "C" being located 3'-wards from "Y". The cleavage site on the upper strand is thus a GUC site (see above). Correspondingly, "R" in the lower strand="A", a "G" correspondingly being located 5'-wards from "R" in the lower strand. This is followed 5'-wards by the further nucleotides from Fragment I according to sequences (l to n) in each case in one of FIG. 1, 3, 4, 5, 6, 7, 8, 9, 11, 12, 13 or 15, i.e. 5 further nucleotides in sequence l, 6 further nucleotides in sequence m and 7 further nucleotides in sequence n. In Fragment III according to FIG. 25, the second with the RNA base-paired fragment, the unpaired "A" on Fragment III is then directly followed from the 5' direction 3'-wards by the nucleotides from Fragment III according to sequences (l to n) in each case in one of FIG. 1, 3, 4, 5, 6, 7, 8, 9, 11, 12, 13 or 15, i.e. 7 further nucleotides in sequence l, 8 further nucleotides in sequence m and 9 further nucleotides in sequence n. Fragment III and Fragment I are the "recognition arms" of the DNA enzyme (see Example 3 below).

The type "10-23" DNA enzyme for sequence n according to FIG. 1 which is particularly preferred for the purposes of the invention would thus have the following sequence, wherein the underlined fragment would be base-paired with the RNA:

ATGTCATGA(=R)-GGCTAGCTACAACGA-GGTTAGGGG (SEQIDNO:249)

This DNA enzyme was named V15 (9/9), wherein the name indicates that the enzyme is oriented towards the GUC site of oligo V15 and the "recognition arms" in each case contain 9 nucleotides (Fragment I and III), for example according to Fragment I and Fragment III of sequence (n) in FIG. 1. The same applies to all DNA enzymes according to subpoints (l to n) in each case in one of FIG. 1, 3, 4, 5, 6, 7, 8, 9, 11, 12, 13 or 15.

The present invention also preferably provides a polynucleotide construct according to the invention, wherein it comprises at least one modified or unmodified ribose, at least one modified or unmodified phosphodiester bond and/or at least one modified or unmodified base.

The present invention also preferably provides an oligonucleotide according to the invention or polynucleotide construct according to the invention, wherein it is bound on a support, in particular a protein, preferably tet-, transportin or ferritin, and/or is packaged in a liposome.

The present invention also preferably provides a cell containing at least one oligonucleotide according to the invention and/or a polynucleotide construct according to the invention.

The present invention also preferably provides a pharmaceutical preparation containing at least one oligonucleotide according to the invention, a polynucleotide construct according to the invention and/or a cell according to the invention, optionally together with a suitable auxiliary substance and/or additive. The pharmaceutical preparations according to the invention may be administered in the form of solutions for injection, drops or juice, as semi-solid dosage forms in the form of granules, tablets, pellets, patches, capsules, dressings or aerosols and, in addition to the at least one subject matter of the invention, they also optionally contain, depending upon the pharmaceutical presentation, excipients, fillers, solvents, diluents, colorants and/or binders. Selection of the auxiliary substances and the quantities thereof which are to be used depends upon whether the pharmaceutical preparation is to be administered orally, perorally, parenterally, intravenously, intraperitoneally, intradermally, intramuscularly, intranasally, buccally, rectally or topically, for example onto infections of the skin, mucous membranes or eyes. Preparations in the form of tablets, coated tablets, capsules, granules, drops, succi and syrups are suitable for oral administration, while solutions, suspensions, easily reconstitutible dried preparations and sprays are suitable for parenteral, topical and inhalatory administration. Subject matters of the invention in a depot in dissolved form or in a dressing, optionally with the addition of skin penetration promoters, are suitable percutaneous administration preparations. Orally or percutaneously administrable formulations may release the subject matters of the invention in delayed manner. The quantity of active substance to be administered to the patient varies as a function of patient weight, mode of administration, the indication and the severity of the condition. 2 to 500 mg/kg of at least one subject matter of the invention are conventionally administered. Especially if the pharmaceutical preparation is to be used for gene therapy, suitable auxiliary substances and additives which it is advisable to use are, for example, a physiological saline solution, stabilizers, proteinase inhibitors, DNAse inhibitors etc.

The present invention also preferably provides a diagnostic aid containing at least one oligonucleotide according to the invention, a polynucleotide construct according to the invention and/or a cell according to the invention, optionally together with suitable additives.

The following definitions apply:
  Pharmaceutical preparation: A substance as defined in Article 1 § 2 of the German Drug Law (Arzneimittelgesetz, AMG). In other words, substances or preparations made from substances which, by application on or in the human or animal body are intended
    1. to cure, alleviate, prevent or diagnose diseases, suffering, bodily injury or sickness symptoms, 2. to diagnose the nature, the state or the functions of the body or mental health conditions,
3. to replace active substances or body fluids produced in the human or animal body,
4. to ward off pathogens, parasites or substances alien to the body or to destroy them or to render them harmless or
5. to influence either the nature, the state or the functions of the body or mental health conditions.

Diagnostic aid: A compound or method which may be used to diagnose a disease.

The present invention also preferably provides the use of at least one oligonucleotide according to the invention, a polynucleotide construct according to the invention and/or a cell according to the invention for the production of a pharmaceutical preparation for the treatment of pain, in particular chronic pain, tactile allodynia, thermally induced pain and/or inflammatory pain.

The present invention also preferably provides the use of at least one oligonucleotide according to the invention, a polynucleotide construct according to the invention and/or a cell according to the invention for the production of a pharmaceutical preparation for the treatment of urinary incontinence; also of neurogenic bladder symptoms; pruritus, tumors, inflammation; in particular VR1 receptor-associated inflammation with symptoms such as asthma; together with any disease symptoms associated with VR1.

The present invention also preferably provides the use of at least one oligonucleotide according to the invention, a polynucleotide construct according to the invention and/or a cell according to the invention for gene therapy, preferably in vivo or in vitro gene therapy. Gene therapy is taken to be a type of therapy in which, by the introduction of nucleic acids into cells, an effector gene product, usually a protein, but also an antisense oligodeoxynucleotide, is expressed. A fundamental distinction is drawn between in vivo and in vitro methods. In in vitro methods, cells are removed from the organism and transfected with vectors ex vivo before subsequently being introduced back into the same organism or a different one. In in vivo gene therapy, vectors, for example for combatting tumors, are administered systemically (for example via the bloodstream) or directly into the tumor.

The present invention also preferably provides a process for the identification of pain-modulating substances, characterized in that identification is made by quantification of the binding of at least one, preferably labeled, oligonucleotide according to the invention or at least one polynucleotide construct onto an RNA.

The present invention also preferably provides a process for the identification of pain-modulating substances comprising the following process steps:
(a) genetic engineering manipulation of at least one cell (test cell) with at least one oligonucleotide according to the invention and/or a polynucleotide construct according to the invention,
(a') parallel genetic engineering manipulation, of at least one identical cell (control cell), which manipulation is either
not carried out,
carried out in parallel with the oligonucleotide or polynucleotide construct, or
carried out with a modified oligonucleotide or polynucleotide construct which is other than one according to the invention,
(b) parallel incubation of a substance to be tested under suitable conditions with at least one test cell and at least one control cell and/or a preparation made from such a cell, which has synthesized at least one receptor protein selected from the vanilloid receptor family, preferably the VR-1 receptor,
(c) measurement of the binding of the test substance onto the protein synthesized by the cells or measurement of at least one functional parameter modified by binding of the test substance onto the receptor protein,
(d) identification of the substances by the extent of the difference between the measured value for the test cell and that for the control cell.

The term pain-modulating here refers to a potentially regulating influence upon physiological pain phenomena, in particular to an analgesic action. The term substance comprises any compound suitable as a pharmaceutical active substance, thus in particular low molecular weight active substances, but also others such as nucleic acids, fats, sugars, peptides or proteins such as antibodies. Incubation under suitable conditions should here be taken to mean that the substance to be investigated is capable of reacting in an aqueous medium for a defined period prior to measurement with the cell or the corresponding preparation. The aqueous medium may be temperature-controlled, for example between 4° C. and 40° C., preferably at room temperature or at 37° C. The incubation time may be varied between a few seconds and several hours, depending upon how the substance interacts with the receptor. Times of between 1 min and 60 min are, however, preferred. The aqueous medium may contain suitable salts and/or buffer systems, such that a pH of between 6 and 8, preferably pH 7.0-7.5 prevails in the medium during incubation. Suitable substances, such as coenzymes, nutrients etc., may additionally be added to the medium. Suitable conditions may readily be established by the person skilled in the art as a function of the substance-receptor interaction which is to be investigated on the basis of his/her experience, the literature or a few simple preliminary tests, so that the clearest possible measured value is obtained from the process. A cell which has synthesized a receptor is a cell which has already endogenously expressed this receptor or one which has been modified by genetic engineering in such a manner that it expresses this receptor and consequently contains the receptor prior to the beginning of the process according to the invention. The cells may be cells from possibly immortalized cell lines or be native cells originating and isolated from tissues, wherein cell aggregation has usually been broken down. The preparation made from these cells in particular comprises cell homogenates, the cytosol, a membrane fraction of the cells with membrane fragments, a suspension of isolated cell organelles etc.

The yardstick which permits the identification of interesting substances is either binding to the receptor, which may, for example, be detected by displacement of a known ligand or by the extent of substance binding, or the modification of a functional parameter due to the interaction of the substance with the receptor. This interaction may in particular involve regulation, inhibition and/or activation of receptors, ion channels and/or enzymes, while modified functional parameters may be, for example, gene expression, ion concentration, pH or membrane potential or modification of enzyme activity or the concentration of secondary messengers. The following definitions apply:
subjected to genetic engineering manipulation: manipulation of cells, tissues or organisms in such a manner that genetic material is introduced or altered therein
endogenously expressed: expression of a protein exhibited by a cell line under suitable culture conditions, without expression of this corresponding protein having been effected by genetic engineering manipulation.

Another preferred embodiment of the present process provides that the cell has already been subjected to genetic engineering manipulation before process steps (a) and (a').

Another preferred embodiment of the present process provides that the genetic engineering manipulation permits the measurement of at least one of the functional parameters modified by the test substance.

Another preferred embodiment of the present process provides that the genetic engineering manipulation results in the expression of a form, not endogenously expressed in the cell, of a member of the vanilloid receptor family, preferably the VR-1 receptor, or in the introduction of a reporter gene.

Another preferred embodiment of the present process provides that binding is measured by the displacement of a known, labeled ligand of a member of the vanilloid receptor family, preferably the VR-1 receptor.

Another preferred embodiment of the present process provides that there is an elapse of not less than 8 h, preferably not less than 12 h, in particular not less than 24 h between the parallel process steps (a) and (a'), and process step (b).

The present invention also preferably provides a process for the diagnosis of clinical conditions which are associated with modified expression of genes of the vanilloid receptor family, which process is characterized in that the diagnosis is made by means of quantification of the binding of an oligonucleotide according to the invention and/or at least one polynucleotide construct onto an RNA.

The oligonucleotides and also the polynucleotide constructs are produced by processes known to the person ordinarily skilled in the art. Nucleotides, in particular also oligonucleotides, are synthesized in the manner of the Merrifield synthesis on an insoluble support (H. G. Gassen et al., Chemical and Enzymatic Synthesis of Gene Fragments (Verlag Chemie, Weinheim 1982)) or in another manner (Beyer/Walter; Lehrbuch der Organischen Chemie, 20th edition, (S. Hirzel Verlag, Stuttgart 1984), pp. 816 et seq.).

The present invention also provides a process for the treatment, in particular treatment for pain, of a non-human mammal or human requiring treatment for pain, in particular chronic pain, by administration of a pharmaceutical preparation according to the invention, in particular such a preparation containing an oligonucleotide according to the invention and/or a polynucleotide construct according to the invention. The invention also provides corresponding processes for the treatment of pruritus and/or urinary incontinence.

The following Examples and Figures are intended to illustrate the invention, but without restricting the subject matter of the invention thereto.

BRIEF DESCRIPTION OF THE DRAWINGS

Figures, Figure and Figure should be regarded as synonymous. In relation to the Figures, the terms subtype and sequence are likewise synonymous. An "X" in the sequences shown denotes any desired complementary nucleotide to the corresponding base on the mRNA of VR1.

FIG. 1 lists general nucleotide sequences starting from an antisense oligodeoxynucleotide sequence against VR1 mRNA from the rat, here frequently designated oligo V15, oligonucleotide no. 15 or V15. Sequences or subtypes (a)-(j) show truncated fragments from this antisense oligodeoxynucleotide sequence. Sequence (k) shows the full-length antisense oligodeoxynucleotide sequence with which the "messenger walk screening" was carried out. Sequences (l)-(n) each shows two nucleotide subsequences (Fragment I and Fragment III) starting from the full-length antisense oligodeoxynucleotide sequence, which each comprises non-overlapping subdomains of this sequence or corresponding sequence thereto, is usually divided at or in the GAC region and, in certain polynucleotide constructs, in particular DNA enzymes, and occurs in two separate domains, the "recognition arms." Subtypes (o)-(q) each shows two nucleotide subsequences (helix I and helix III) starting from the full-length antisense oligodeoxynucleotide sequence (in this case as RNA), which each comprises non-overlapping subdomains of this sequence or a corresponding sequence thereto, is usually divided at or in the GAC region and, in certain polynucleotide constructs, in particular ribozymes, and occurs in two separate domains, the "recognition arms."

FIG. 2 shows the sequence of an antisense deoxyoligonucleotide against human VR1 corresponding in position on the mRNA to oligo V15 in FIG. 1. With regard to type and general content, subtypes or sequences (a)-(k) correspond to that already described in relation to FIG. 1.

FIG. 3 shows a list of general nucleotide sequences starting from an antisense oligodeoxynucleotide sequence against VR1 mRNA from the rat, here frequently designated oligo V30, oligonucleotide no. 30 or V30. The type and general content of the subtypes correspond to that already described in relation to FIG. 1.

FIG. 4 shows the sequence of an antisense deoxyoligonucleotide against human VR1 corresponding in position on the mRNA to oligo V30 in FIG. 3. With regard to type and general content, subtypes (a)-(q) correspond to that already described in relation to FIG. 1.

FIG. 5 lists general nucleotide sequences starting from an antisense oligodeoxynucleotide sequence against VR1 mRNA from the rat, here frequently designated oligo V32, oligonucleotide no. 32 or V32. The type and general content of the subtypes correspond to that already described in relation to FIG. 1.

FIG. 6 shows the sequence of an antisense deoxyoligonucleotide against human VR1 corresponding in position on the mRNA to oligo V32 in FIG. 5. With regard to type and general content, subtypes (a)-(q) correspond to that already described in relation to FIG. 1.

FIG. 7 lists general nucleotide sequences starting from an antisense oligodeoxynucleotide sequence against VR1 mRNA from the rat, here frequently designated oligo V26, oligonucleotide no. 26 or V26. The type and general content of the subtypes correspond to that already described in relation to FIG. 1.

FIG. 8 shows the sequence of an antisense deoxyoligonucleotide against human VR1 corresponding in position on the mRNA to oligo V26 in FIG. 7. With regard to type and general content, subtypes (a)-(q) correspond to that already described in relation to FIG. 1.

FIG. 9 lists general nucleotide sequences starting from an antisense oligodeoxynucleotide sequence against VR1 mRNA from the rat, here frequently designated oligo V2, oligonucleotide no. 2 or V2. The type and general content of the subtypes correspond to that already described in relation to FIG. 1.

FIG. 10 shows the sequence of an antisense deoxyoligonucleotide against human VR1 corresponding in position on the mRNA to oligo V2 in FIG. 9. With regard to type and general content, subtypes (a)-(k) correspond to that already described in relation to FIG. 1.

FIG. 11 lists general nucleotide sequences starting from an antisense oligodeoxynucleotide sequence against VR1 mRNA from the rat, here frequently designated oligo V16, oligonucleotide no. 16 or V16. The type and general content of the subtypes correspond to that already described in relation to FIG. 1.

FIG. 12 shows the sequence of an antisense deoxyoligonucleotide against human VR1 corresponding in position on the mRNA to oligo V16 in FIG. 11. With regard to type and general content, subtypes (a)-(q) correspond to that already described in relation to FIG. 1.

FIG. 13 lists general nucleotide sequences starting from an antisense oligodeoxynucleotide sequence against VR1 mRNA from the rat, here frequently designated oligo V28, oligonucleotide no. 28 or V28. The type and general content of the subtypes correspond to that already described in relation to FIG. 1.

FIG. 14 shows the sequence of an antisense deoxyoligonucleotide against human VR1 corresponding in position on the mRNA to oligo V28 in FIG. 13. With regard to type and general content, subtypes (a)-(k) correspond to that already described in relation to FIG. 1.

FIG. 15 lists general nucleotide sequences starting from an antisense oligodeoxynucleotide sequence against VR1 mRNA from the rat, here frequently designated oligo V4, oligonucleotide no. 4 or V4. The type and general content of the subtypes correspond to that already described in relation to FIG. 1.

FIG. 16 shows the sequence of an antisense deoxyoligonucleotide against human VR1 corresponding in position on the mRNA to oligo V4 in FIG. 15. With regard to type and general content, subtypes (a)-(k) correspond to that already described in relation to FIG. 1.

FIG. 18 is a plot of the percentage of the uncut mRNA after the RNase H assay with the individual ODNs. Each value is the mean of at least two experiments, such that the standard deviation does not ever exceed 10%. The antisense oligodeoxynucleotides against the 15th and 30th GUC sites bind most efficiently to the VR1 mRNA, such that the latter is respectively 88±4 and 97±1% degraded by the RNase H (oligo V15 and oligo V30).

ATGTCATGA(=R)-GGCTAGCTACAACGA-GGTTAGGGG(SEQ ID NO:249)

This DNA enzyme would be named V15 (9/9), wherein the name indicates that the enzyme is oriented towards the GUC site of oligo V15 and the "recognition arms" in each case contain 9 nucleotides (Fragment I and III), for example according to Fragment I and Fragment III of sequence (n) in FIG. 1. The same applies to all DNA enzymes according to sequences (l) to (n) in each case in one of FIG. 1, 3, 4, 5, 6, 7, 8, 9, 11, 12, 13 or 15.

Figure 27:
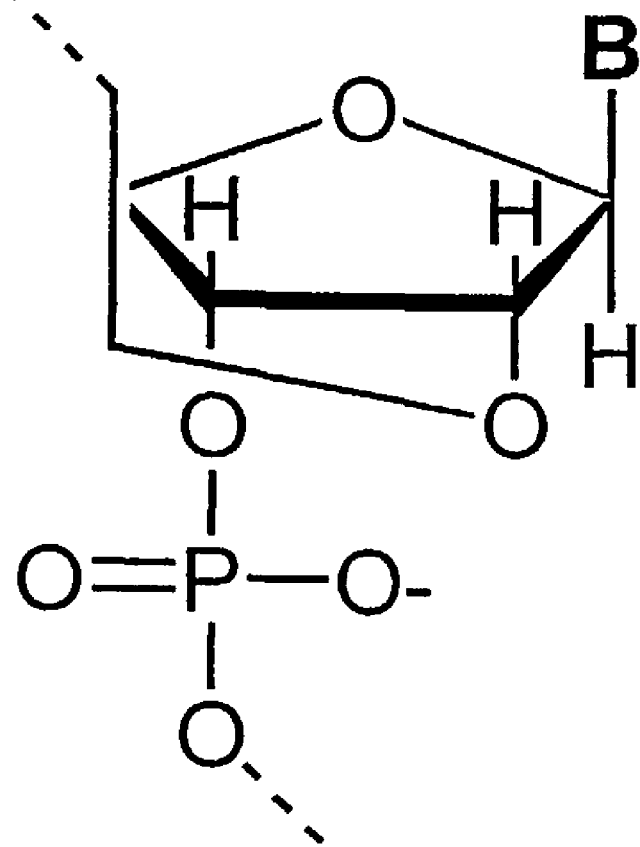

FIG. 27 is a schematic diagram of a "locked nucleic acid" (LNA).

EXAMPLES

Example 1

Identification of Generally Suitable Restriction Sites

The first step in the antisense and ribozyme strategy is to identify accessible sites on the mRNA for binding oligonucleotides, in particular ribozymes. To this end, the VR1 mRNA had to be investigated for such restriction sites. Analysis of the VR1 mRNA revealed the following potential recognition sites for ribozymes in the coding domain:

```
33 X GT(U)C sequences,
28 X GT(U)T sequences, and
12 X GT(U)A sequences.
```

In order to determine the accessible sites on the VR1 mRNA, in a first step, three independent nucleotide mixtures with the following sequence were synthesized:

```
Mixture 1: NNNAACNNN "GUU library,"
Mixture 2: NNNCACNNN "GUA library," and
Mixture 3: NNNGACNNN "GUC library."
```

These were used consecutively in an RNase H experiment and it was found that appreciable degradation of the VR1 mRNA was observed only with the GUC library. Thus, of the potential target sequences for ribozymes, the 33 GUC sites in the VR1 mRNA are the most readily accessible and they were used for further analyses.

Example 2

Identification of the Most Effective Antisense Oligodeoxynucleotides

Messenger Walk Screening

Figure 17:
FIG. 17 shows the result of messenger walk screening. In each track there can be seen, in addition to the upper band of the uncut substrate, the two product bands of the cut mRNA together with several non-specific bands. The figure shows the VR1 mRNA after degradation by RNase H in the presence in each case of one of 33 antisense oligonucleotides (oligo V1 to oligo V33). In each track there can be seen, in addition to the upper band of the uncut substrate, the two product bands of the cut mRNA together with several non-specific bands. Track 1: VR1 mRNA, tracks 2-34: RNase H assay with antisense oligodeoxynucleotides against the 33 GUC sites of VR1 mRNA (oligo V1 to oligo V33).

In order to identify mRNA domains which are accessible to antisense oligodeoxynucleotides, the mRNA was systematically screened with ODNs in an RNase H assay (messenger walk screening). The ODNs were 18 nucleotides in length and contained a central GAC sequence, which is reverse complementary to GUC sequences in the mRNA. This triplet was selected as the target as it provided good results and may be used in a second step to develop hammerhead ribozymes and DNA enzymes. In total, 33 ODNs, designated V1 to V33, were tested against all the GUC sites of the VR1 mRNA. The ODNs were systematically screened for their suitability by the addition in each case of one ODN and RNase H to the mRNA. RNase H cuts formed DNA/RNA duplexes wherever an oligonucleotide can bind to the mRNA (FIG. 17).

In Vitro Transcription of VR1 mRNA

First of all, the cDNA of the vanilloid receptor was cloned into the vector pcDNA3.1 (+) from Invitrogen. Then, in vitro transcription of the mRNA was performed using the RiboMAX Large Scale RNA Production System—T7 from Promega in accordance with the manufacturer's instructions.

RNase H Assay

An RNase H assay was performed to test whether an antisense oligodeoxynucleotide had bound to the mRNA. To this end, the VR1 mRNA (100 mM) was incubated with a five-fold excess of the ODNs in a total volume of 10 µl in 40 mM tris/HCl pH 7.2, 4 mM $MgCl_2$, 1 mM DTT and 150 mM NaCl for 7.5 minutes at 37° C. in the presence of 0.4 unit of RNase H (from Promega). The reactions were terminated by addition of EDTA (65 mM final concentration). The samples were separated on a 1.5% agarose gel and stained with ethidium bromide (1 µg/ml) for 20 minutes. The gels were photographed with the Gel Doc 2000 Gel Documentation System from Biorad and evaluated with Quantity One software.

FIG. 17 shows the result of messenger walk screening. In each track there can be seen, in addition to the upper band of the uncut substrate, the two product bands of the cut mRNA together with several non-specific bands.

Figure 18:
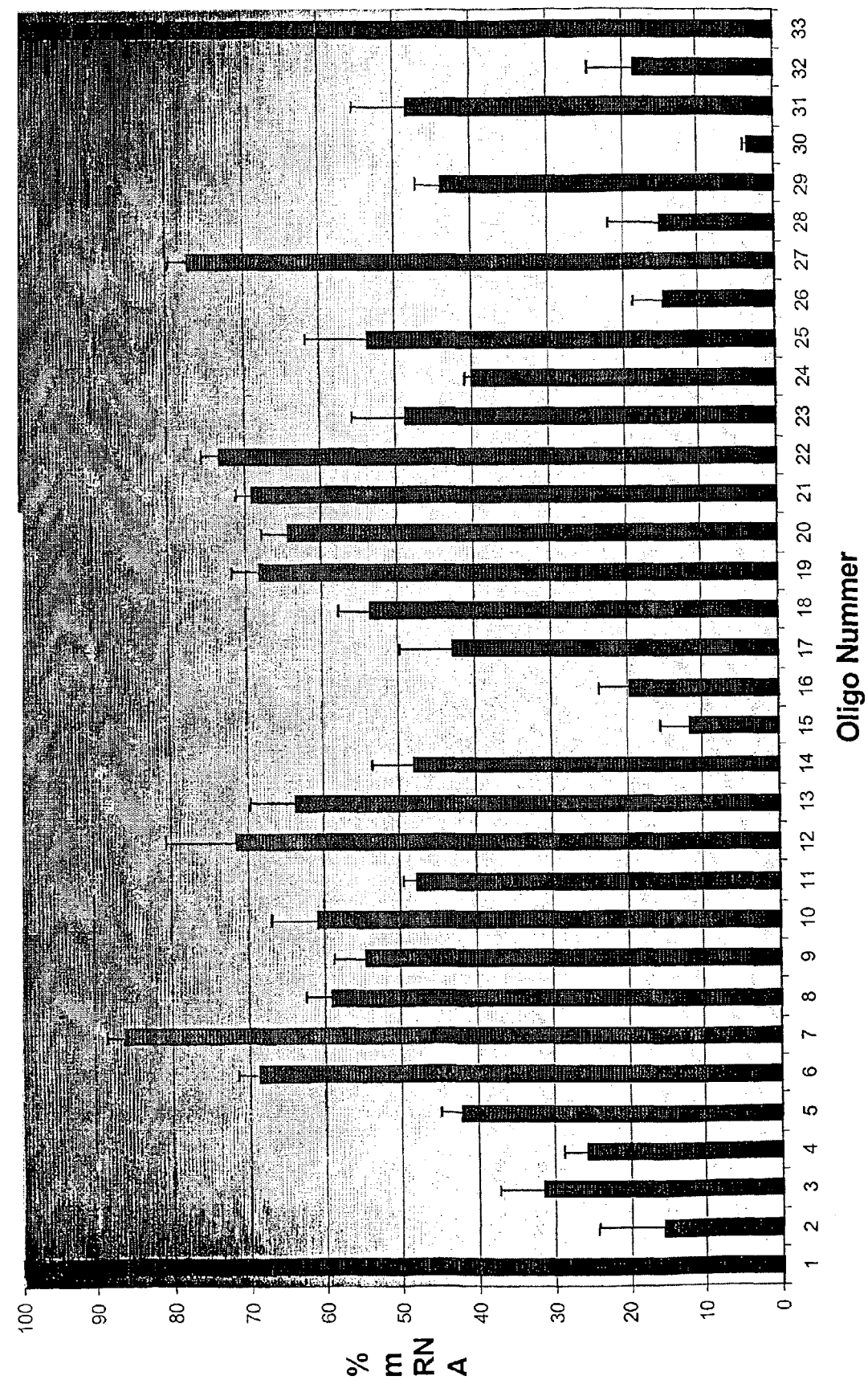
FIG. 18 shows quantitative evaluation of messenger walk screening.

Quantification of RNA degradation revealed that the most effective antisense oligonucleotide (oligo no. 30 (V30)) was able specifically to cut/cleave more than 90% of the VR1 mRNA when used in a five-fold excess relative to the target mRNA (FIG. 18).

The intensities of the individual bands were evaluated. FIG. 18 is a plot of the percentage of the uncut mRNA for the individual ODNs after the RNase H assay. The antisense oligodeoxynucleotides against the 15th and 30th GUC sites (oligo V15 and oligo V30) bind most efficiently to the VR1 mRNA, such that the latter is respectively 88±4 and 97±1% degraded by the RNase H.

The sequences of the antisense oligodeoxynucleotides most effective in this test are shown in FIGS. 1, 3, 5, 7, 9, 11, 13 and 15, wherein inter alia preferential attention was paid to those designated oligo V15 (FIG. 1) and oligo V30 (FIG. 3).

Oligodeoxynucleotides in which every fifth and six base (or in the event that these are identical, two adjacent bases) are swapped were synthesized and used in the following experiments as mismatch controls for these antisense oligodeoxynucleotides. The sequences of the control (mismatch) oligodeoxynucleotides are:

```
Oligo V15ctrl.: CAT GCT ATG AGC GTT   (SEQ ID NO:250)
GAG
Oligo V30ctrl.: ATC TGT TTG AGC GTC   (SEQ ID NO:251)
TAC
```

Figure 19:
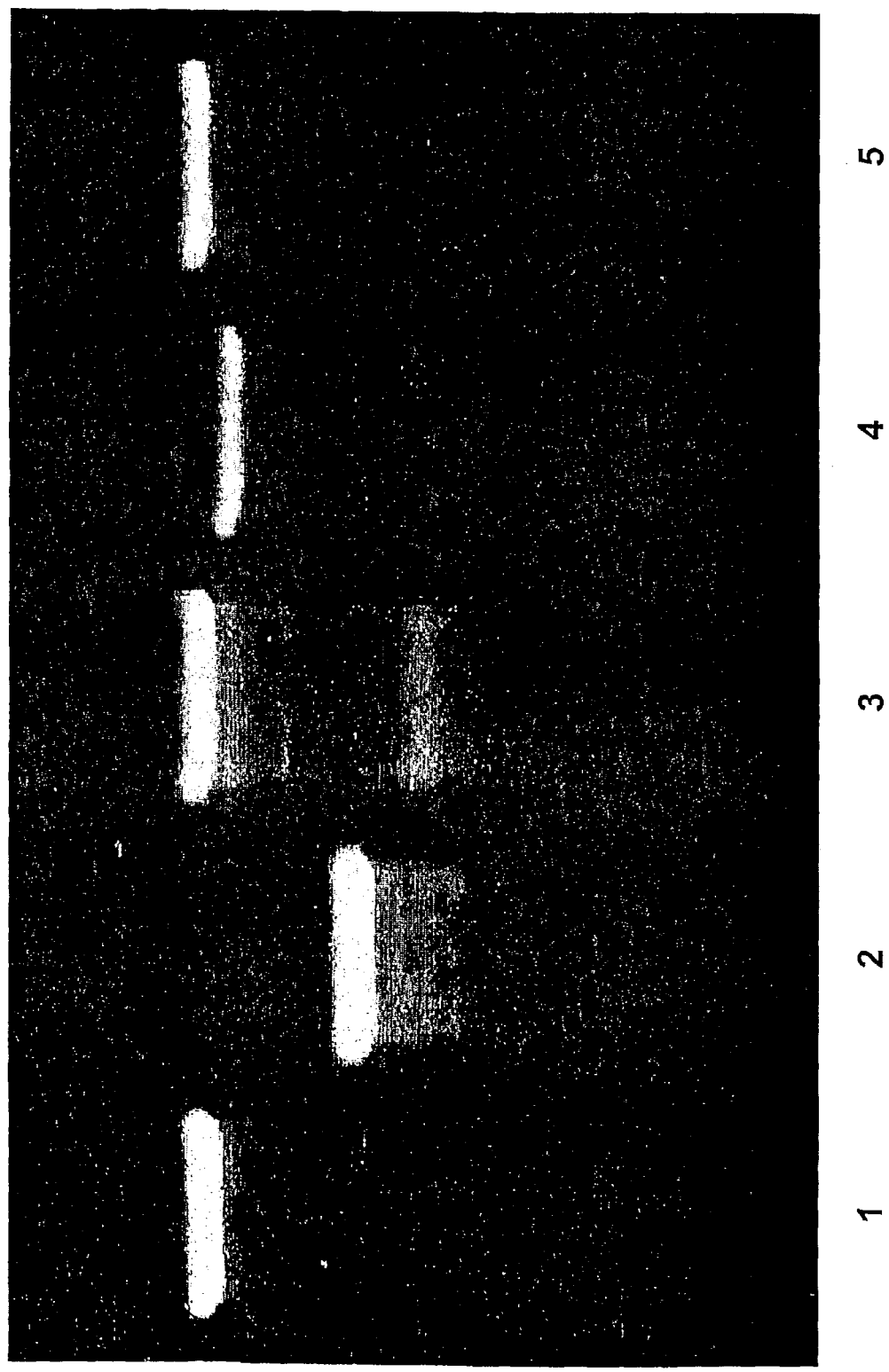
FIG. 19 is an image of a gel after RNase H assay with oligonucleotides V15, V15ctrl. (mismatch), V30 and V30ctrl. (mismatch). The Figure shows VR1 mRNA (track 1) and RNase H assay with oligodeoxynucleotides V15, V15ctrl., V30 and V30ctrl. (tracks 2-5).

The RNase H assay was performed with the oligonucleotides V15, V15ctrl., V30 and V30ctrl. for control purposes (see FIG. 19). As anticipated, the RNA is degraded only with the antisense ODNs, but not with the mismatch controls, as the latter do not bind to the mRNA.

Summary

By using the RNase H assay with antisense oligodeoxynucleotides against all the GUC triplets of the VR1 mRNA, it was possible to identify oligodeoxynucleotides against the GUC triplets (2, 4, 15, 16, 26, 28, 30 and 32), in particular the 15th and 30th which were the ODNs with the best binding properties. These oligodeoxynucleotides and the two mismatch controls are thus available for testing in an animal model and for other uses.

The human sequences according to FIGS. 2, 4, 6, 8, 10, 12, 14, 16, which correspond in position to those found in the rat sequences, are of particular interest. Rat and human mRNAs are highly homologous (probably also in terms of folding) and it is thus clear that restriction sites identified as readily accessible on rat mRNA are also of interest for humans. Particularly preferred sequences here are those which also exhibit the GUC triplet, FIGS. 4, 6, 8 and 12, and, due to the location similar to that in rats, also those corresponding to V15 and V30 according to FIGS. 2 and 4.

Example 3

Ribozymes and DNA Enzymes

On the basis of the identified most effective binding sites, corresponding ribozymes and DNA enzymes were also investigated.

Figure 20:
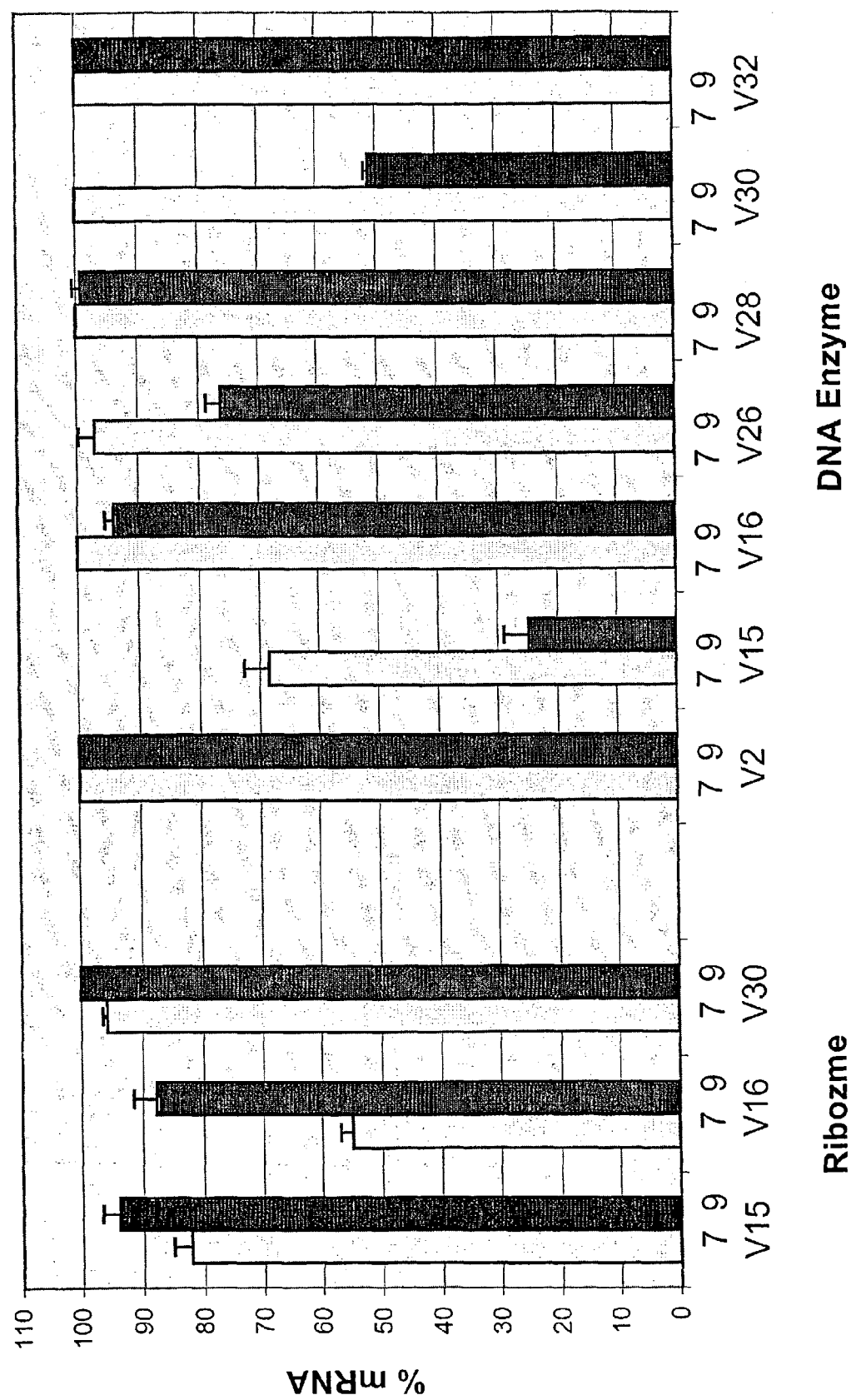
FIG. 20 shows the quantitative evaluation of cleavage of mRNA by ribozymes and DNA enzymes under "single turnover" conditions.
Figure 24:
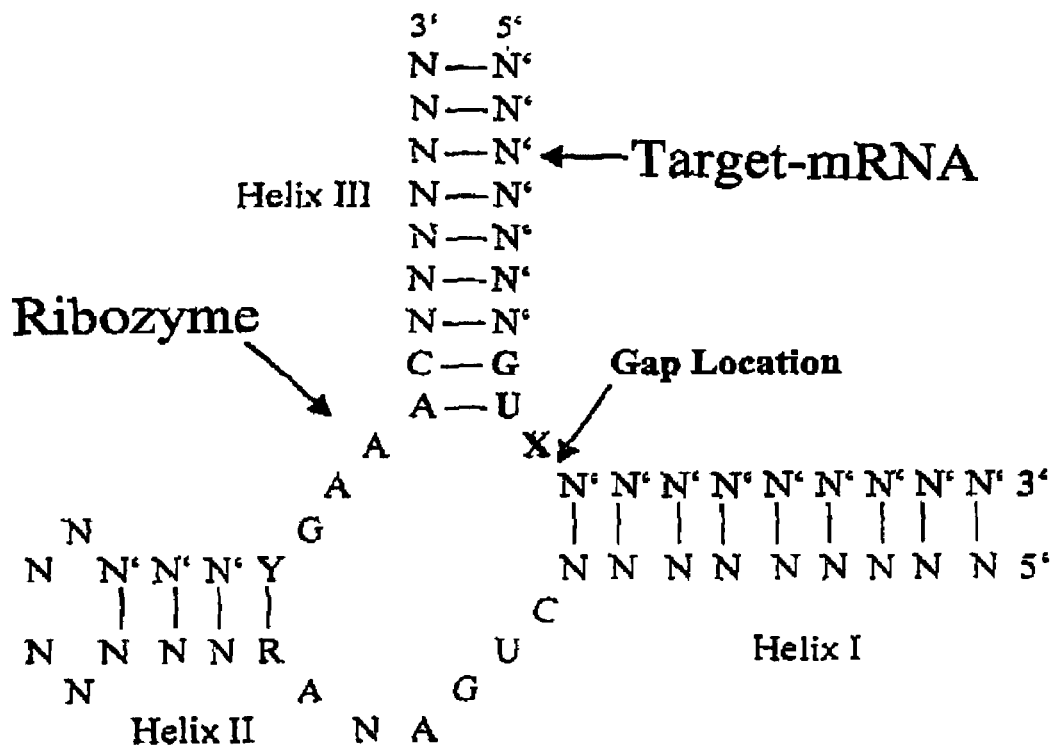
FIG. 24 is a general diagram of a "hammerhead" ribozyme with the "recognition arms" helix I and helix III, into which the helices I and III according to subtypes (o)-(q) in one of FIG. 1, 3, 4, 5, 6, 7, 8, 9, 11, 12, 13 or 15 are inserted, in order to obtain the inventive hammerhead ribozymes (see description relating to FIG. 1). The fragment helix I here replaces in each case in one of FIG. 1, 3, 4, 5, 6, 7, 8, 9, 11, 12, 13 or 15 the desired nucleotides in helix I according to FIG. 24 in such a manner that the first nucleotide on the 3' end of helix I in each case in one of FIG. 1, 3, 4, 5, 6, 7, 8, 9, 11, 12, 13 or 15 replaces the first desired nucleotide "N" on the 3' end of helix I of FIG. 24 and the following desired nucleotides "N" in helix I, FIG. 24 towards the 5' end are replaced by the nucleotides which are shown in one of sequences (o) to (q) of helix I in each case in one of FIG. 1, 3, 4, 5, 6, 7, 8, 9, 11, 12, 13 or 15. The nucleotides "A" and "C" on the 5' end of helix III in one of FIG. 1, 3, 4, 5, 6, 7, 8, 9, 11, 12, 13 or 15 in each case replace the nucleotides "A" and "C" in helix III in FIG. 24 and the following desired nucleotides "N" in helix III, FIG. 24 are replaced in the 5' end direction by the nucleotides which are shown in one of sequences (o)-(q), helix III, in each case in one of FIG. 1, 3, 4, 5, 6, 7, 8, 9, 11, 12, 13 or 15.
Figure 25:
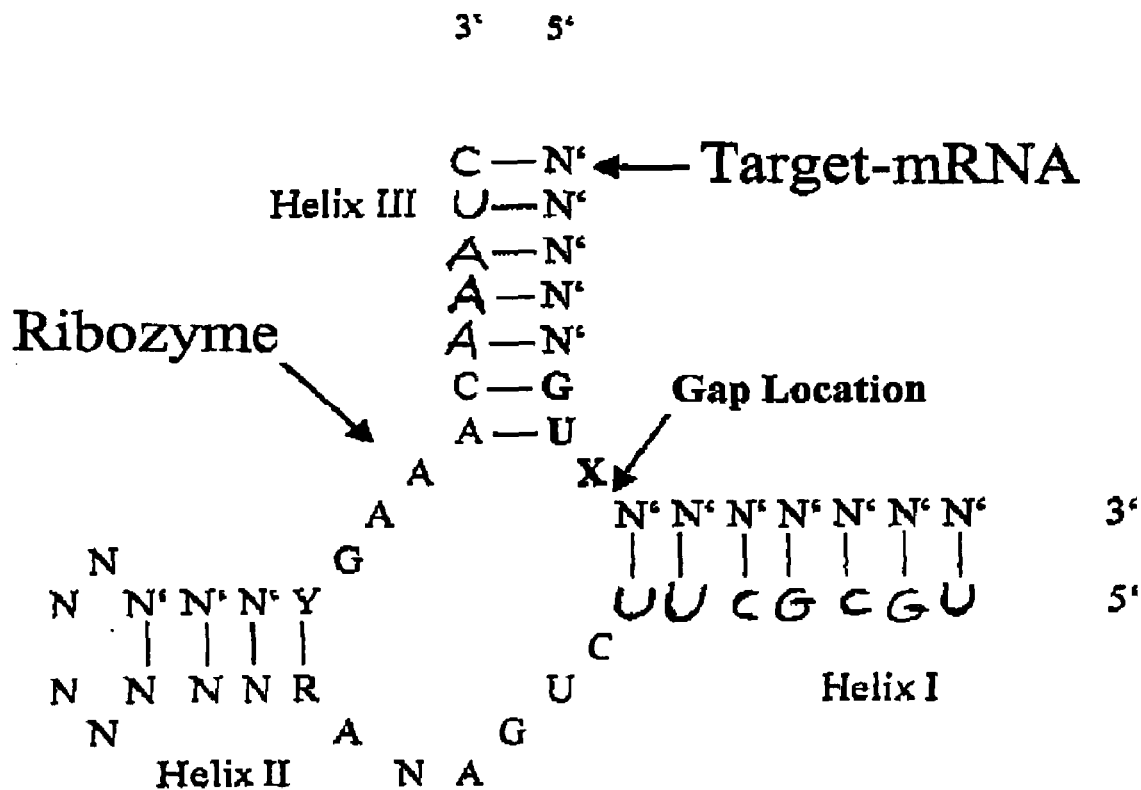
FIG. 25 shows a specific example of the preparation of the (particularly preferred) "hammerhead" ribozyme V16 (7/7) according to FIG. 24 and FIG. 11. The designation ribozyme V16 (7/7) here means that the enzyme is oriented towards the GUC site of oligo V16 and contains 7 nucleotides in each of the "recognition arms" (helix I and helix III), in this case according to helix I and helix III of sequence (o) in FIG. 11. The same applies to all ribozymes according to sequences (o to q) in each case in one of FIG. 1, 3, 4, 5, 6, 7, 8, 9, 11, 12, 13 or 15.
Figure 26:
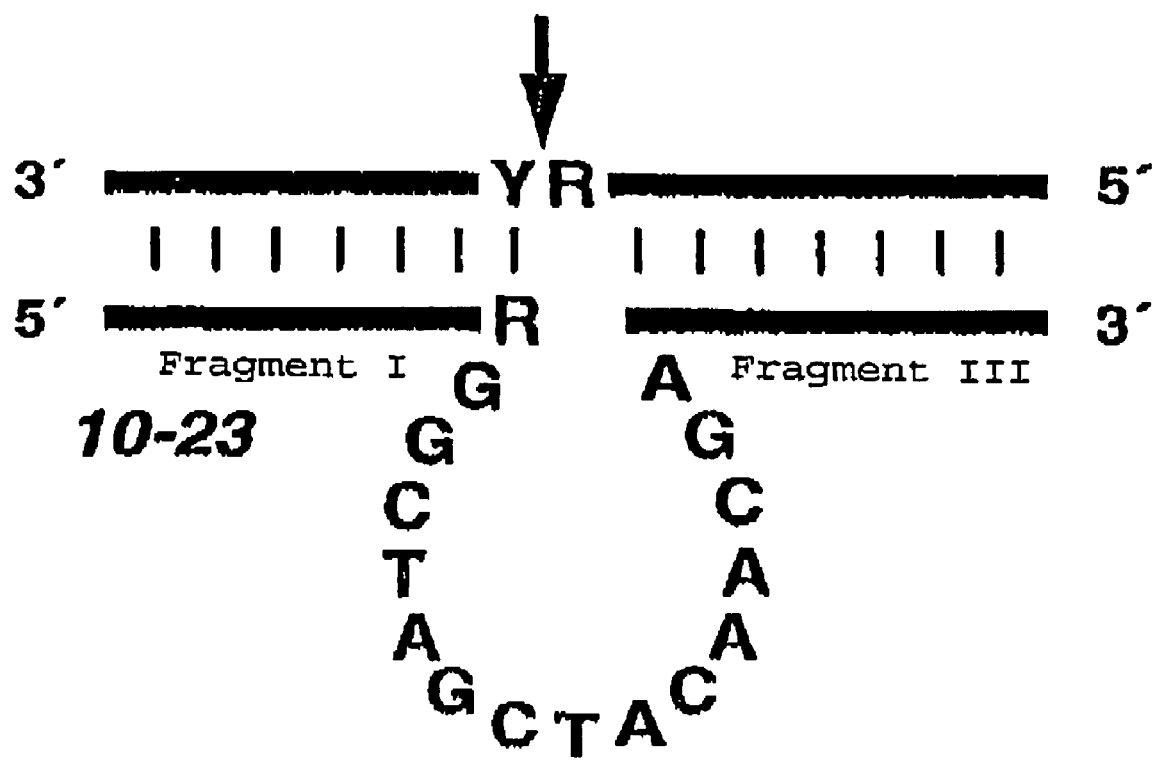
FIG. 26 is a diagram of a type "10-23" DNA enzyme according to Santoro et al., 1997, FIG. 2, p. 4264; the upper strand marked with an arrow is the RNA strand to be cleaved, the arrow showing the cleavage site, while the lower strand is a representation of the DNA enzyme. With regard to the present application, in the upper strand the "Y"="U" and the "R"="G", a "C" being located 3'-wards from "Y". The cleavage site on the upper strand is thus a GUC site (see above). Correspondingly, "R" in the lower strand="A", a "G" correspondingly being located 5'-wards from "R" in the lower strand. This is followed 5'-wards by the further nucleotides from Fragment I according to sequences (l) to (n) in each case in one of FIG. 1, 3, 4, 5, 6, 7, 8, 9, 11, 12, 13 or 15, i.e. 5 further nucleotides in sequence l, 6 further nucleotides in sequence m and 7 further nucleotides in sequence n. In Fragment III according to FIG. 25, the second with the RNA base-paired fragment, the unpaired "A" on Fragment III is then directly followed from the 5' direction 3'-wards by the nucleotides from Fragment III according to sequences (l) to (n) in each case in one of FIG. 1, 3, 4, 5, 6, 7, 8, 9, 11, 12, 13 or 15, i.e. 7 further nucleotides in sequence l, 8 further nucleotides in sequence m and 9 further nucleotides in sequence n. Fragment III and Fragment I are the "recognition arms" of the DNA enzyme (see Example 3). The type "10-23" DNA enzyme for sequence (n) according to FIG. 1 would thus have the following sequence, wherein the underlined fragment would be base-paired with the RNA.

"Hammerhead" ribozymes and type "10-23" DNA enzymes (Santoro et al., 1997) were constructed against the mRNA sites which were accessible to ODNs. The length of the "recognition arms" was 7 or 9 nucleotides on each side. Quantitative evaluation of mRNA cleavage/restriction under "single turnover" conditions (10-fold excess of ribozymes and DNA enzymes) revealed after 20 minutes at 37° C. that ribozymes with shorter "recognition arms" (helix I and helix III) are more active, while in turn in DNA enzymes, those with longer "arms" (Fragment I and Fragment III) are more active (FIG. 20). FIG. 24 is a schematic representation of a ribozyme with the helices I and III, while FIG. 25 shows a specific example. This may be seen for a 10-23 DNA enzyme (5'-end (Fragment I) and 3'-end (Fragment III) from the catalytic motif) in Santoro et al. (1997, p. 4264, FIG. 2) (see also FIG. 26) with the description of the Figures).

Experiments with ribozymes and DNA enzymes were carried out in 50 mM tris/HCl, pH 7.5 and 10 mM $MgCl_2$ at 37° C. In the "single turnover" experiments, the ribozymes and DNA enzymes were used in a 10-fold excess. In "multiple turnover" experiments, the substrate mRNA was used in a 10-fold excess.

"Single Turnover" Kinetics

Figure 21:
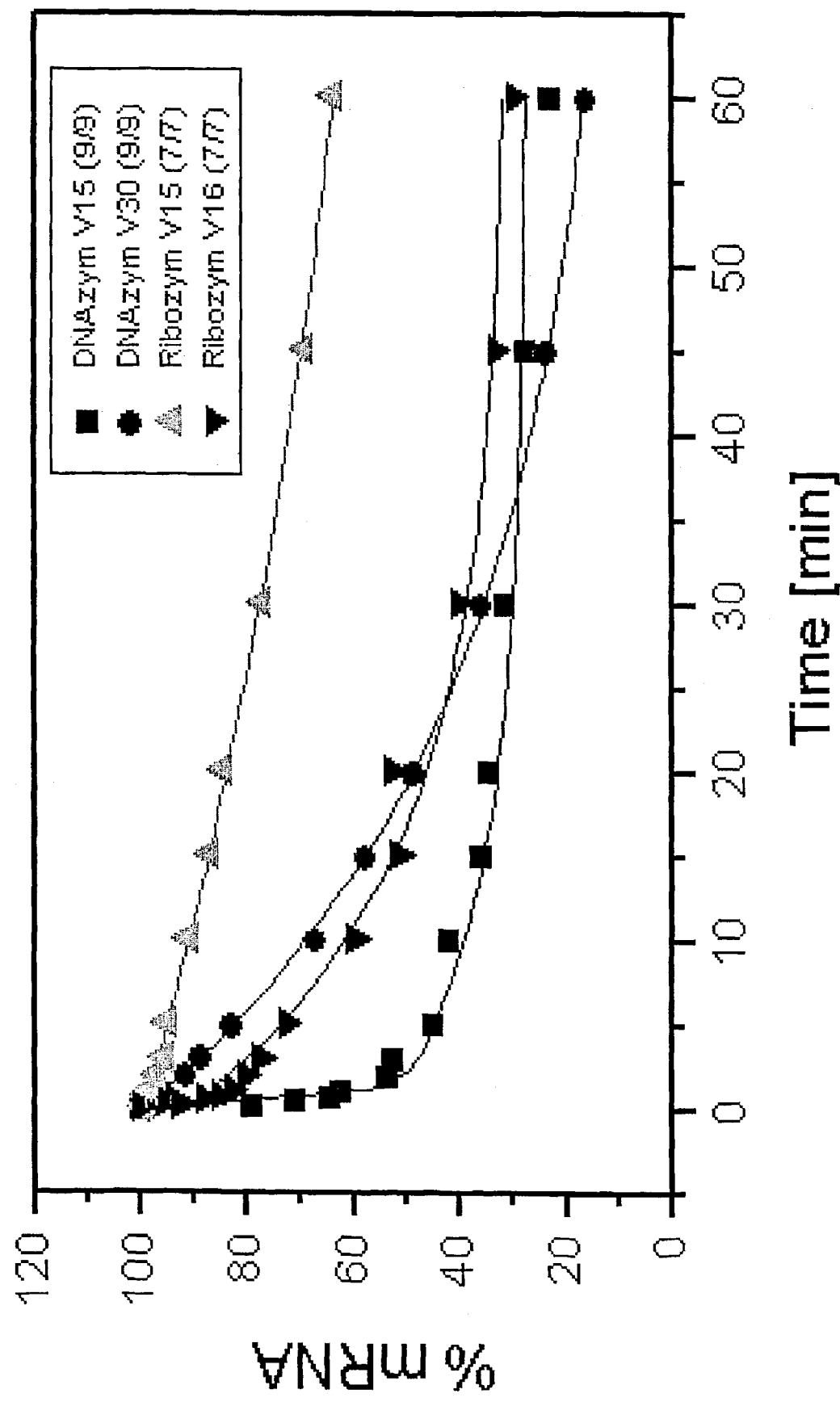
FIG. 21 shows the kinetics of VR1 mRNA cleavage by ribozymes and DNA enzymes under "single turnover" conditions.

A kinetic analysis under "single turnover" conditions was carried out for the two most effective ribozymes and DNA enzymes (FIG. 21). The data are shown in Table 1. DNA enzyme V15 (9/9) (see description of FIG. 26), which cuts the mRNA with biphasic kinetics, has the highest rate (rate constant), followed by ribozyme V16 (7/7) (see FIG. 25), DNA enzyme V30 (9/9) and the slowest ribozyme V15 (7/7). The designation ribozyme V15 (7/7), for example, here means that the enzyme is oriented towards the GUC site of oligo V15 and contains 7 nucleotides in each of the "recognition arms" (helix I and helix III), for example according to Fragment I and Fragment III of subtype (I) in FIG. 1.

TABLE 1

Kinetics data for ribozymes and DNA enzymes against VR1 mRNA under "single turnover" conditions.

|  | $A_1$ | $k_1$ [$min^{-1}$] | $A_2$ | $k_2$ [$min^{-1}$] | $A_\infty$ |
|---|---|---|---|---|---|
| DNAzyme V15(9/9) | 0.43 ± 0.05 | 2.3 ± 0.5 | 0.34 ± 0.04 | 0.07 ± 0.01 | 0.21 ± 0.03 |
| DNAzyme V30(9/9) | 0.90 ± 0.02 | 0.042 ± 0.002 | — | — | 0.08 ± 0.02 |
| Ribo V15(7/7) | 0.51 ± 0.09 | 0.023 ± 0.007 | — | — | 0.49 ± 0.09 |
| Ribo V16(7/7) | 0.58 ± 0.02 | 0.077 ± 0.008 | — | — | 0.34 ± 0.03 |

"Multiple Turnover" Kinetics

Figure 22:
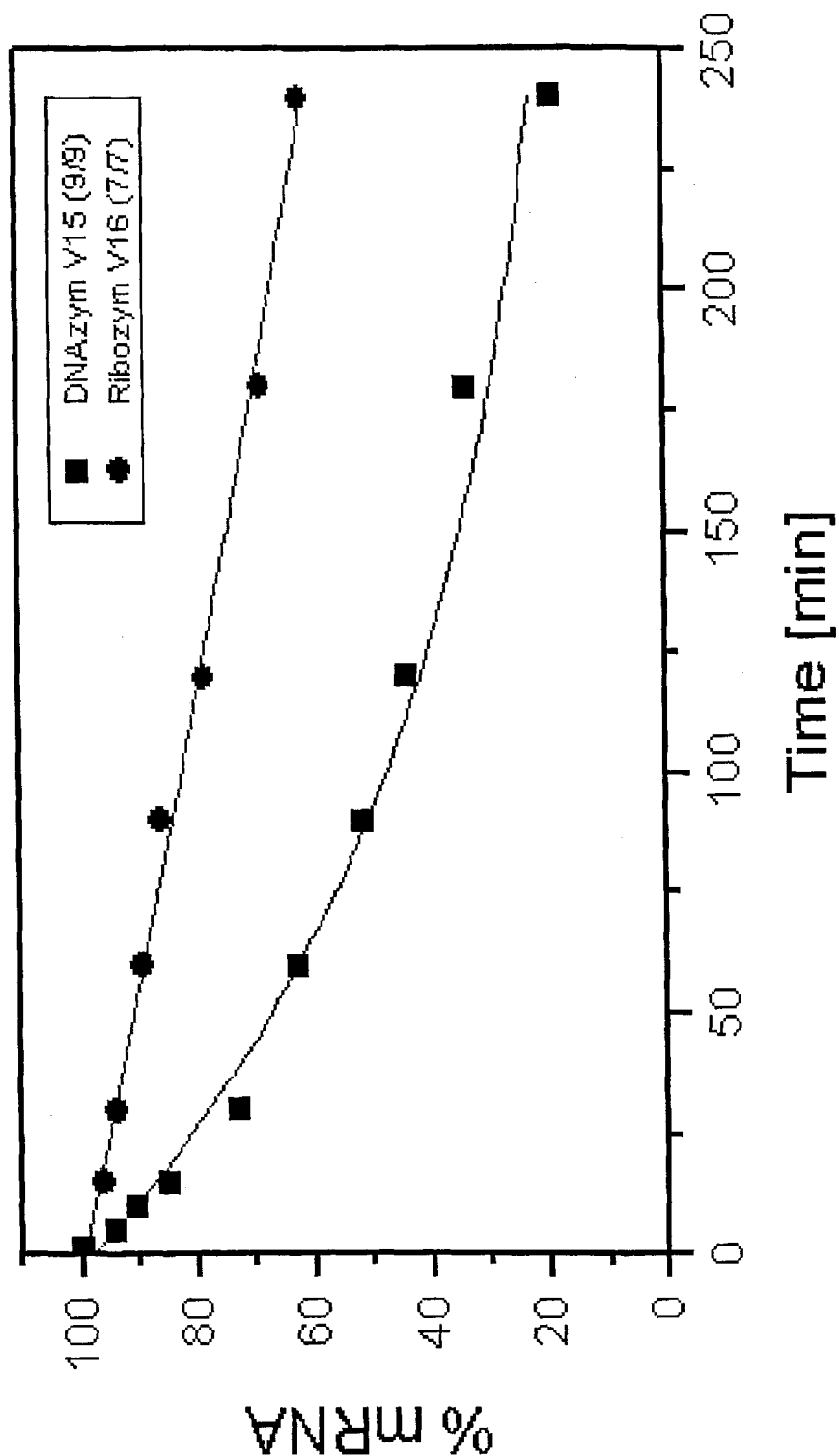
FIG. 22 shows the kinetics of VR1 mRNA cleavage by ribozymes and DNA enzymes under "multiple turnover" conditions.
Figure 23:
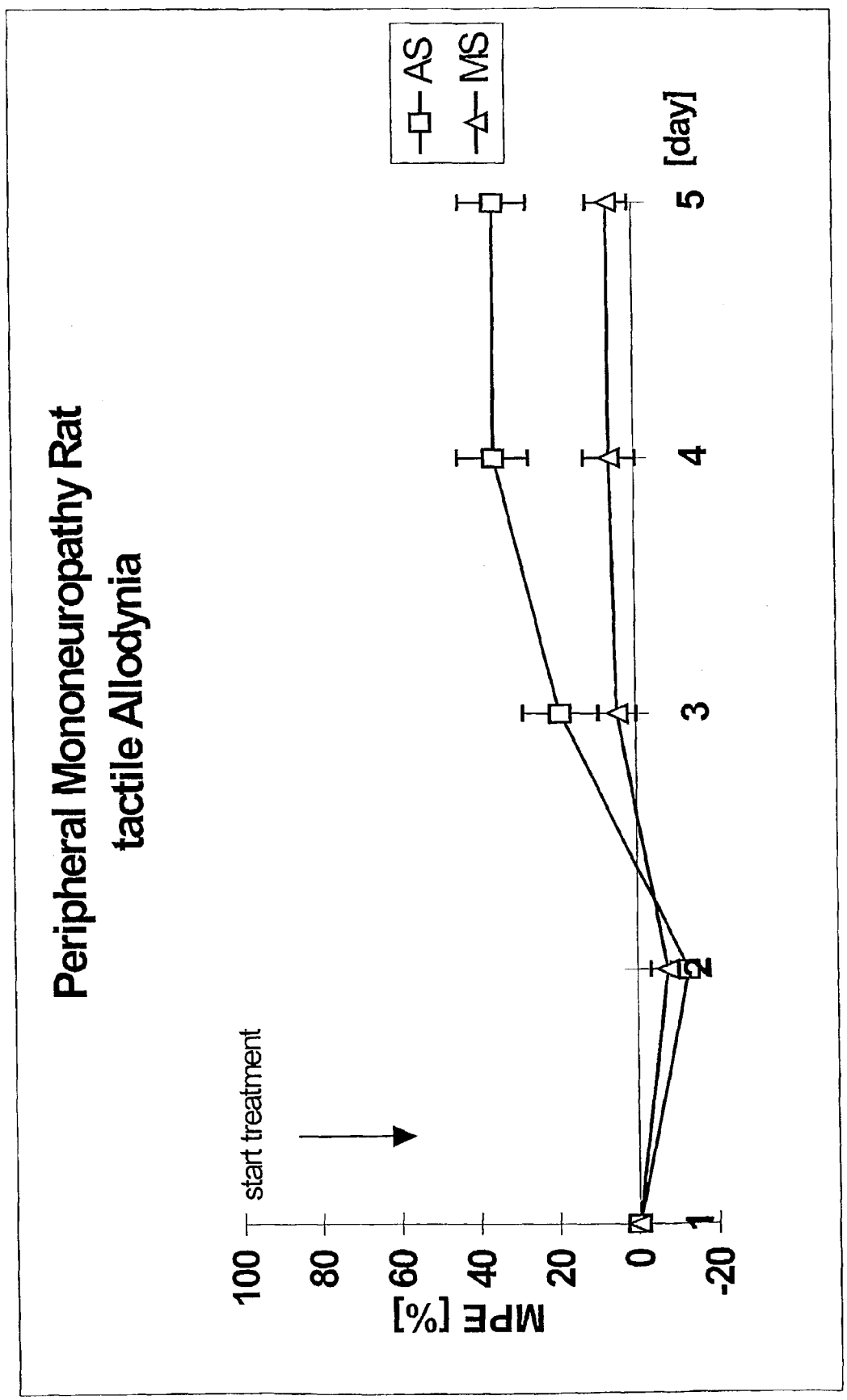
FIG. 23 shows an estimation of tactile allodynia during treatment by VR1-antisense (AS) oligodeoxynucleotides and mismatch (MS) oligodeoxynucleotides (V15 and V15ctrl.).

FIG. 22 shows the cleavage of the mRNA under "multiple turnover" conditions (10-fold substrate excess). Again DNA enzyme V15 (9/9) has a higher apparent rate (rate constant) (by a factor of 3.4) than ribozyme V16 (7/7) (Table 2).

TABLE 2

Kinetics data for ribozymes and DNA enzymes against VR1 mRNA under "multiple turnover" conditions

|  | k [$min^{-1}$] |
|---|---|
| DNAzyme V15 (9/9) | $(6.5 ± 0.6)*10^{-3}$ |
| Ribo V16 (7/7) | $(1.9 ± 0.2)*10^{-3}$ |

Example 4

In Vivo Experiments

Spinal nerve ligatures were placed as described by Kim & Chung (1992) on the left L5/L6 spinal nerves of 20 male Sprague-Dawley rats. At the same time, spinal catheters were implanted as described by Pogatzki et al. (2000). Four to six days after the operation, the tactile threshold baseline (withdrawal thresholds) was measured on the ipsilateral and contralateral hind paw using an electronic von Frey anaesthesiometer (IITC Life Science, USA). Correct positioning of the spinal catheter was confirmed by administering lidocaine (10 µl, 2%), which resulted in transient paralysis of both hind limbs. After the test and measurement of the baseline, 45 µg of VR-1 antisense oligonucleotides (AS, n=10) or mismatch oligonucleotides (MS, n=10) in 0.9% NaCl were in each case given once on the first day and b.i.d. on the following 4 days. The tactile withdrawal thresholds were measured 30 minutes after the first daily administration of oligo. The results are stated as a percentage of the maximum possible effect (%MPE) on the ipsilateral side, the base line being taken as 0% and the withdrawal threshold of a control group as 100% MPE. The antisense oligo used was V15 (FIG. 1, subtype k), while the mismatch oligo was V15ctrl., as already described above.

Treating mononeuropathic rats with antisense, but not with mismatch, oligodeoxynucleotides brought about a reduction in tactile allodynia beginning on the third day of treatment, with a plateau being reached on days 4 and 5 of treatment. There was no effect on the withdrawal thresholds of the contralateral hind paw.

Example 5

"Locked Nucleotides"/Oligonucleotides Protected from Degradation and Oligonucleotide Constructs Various different oligonucleotides according to the invention were produced, in particular according to subgroup (k) of FIG. 1 and, in some cases, also FIG. 3. Most of these were LNA constructs which were obtained from PROLIGO, in Boulder, Colo., and in which LNAs were located at various sites (see Table 3). An unmodified oligonucleotide according to subgroup (k) of FIG. 1 was also synthesized and a phosphorothioate corresponding in terms of base sequence was obtained from MWG Biotech AG in Ebersberg, Germany.

TABLE 3

List of oligonucleotides used

| Name | Sequence | % mRNA cleavage | % LNA content | DNA gap |
|---|---|---|---|---|
| DNA 1 | Catgtcatgacggttagg (SEQ ID 11) | 90 ± 1 | 0 | — |
| PS | CATGTCATGACGGTTAGG (SEQ ID 11) | 71 ± 7 | 0 | — |
| | Mixed | | | |
| LNA 1 | catgTcaTgcggTtagg* (SEQ ID 11) | 12 ± 2 | 16 | 5 |
| LNA 2 | CatgTcaTgcggTtagg (SEQ ID 11) | 11 ± 9 | 22 | 5 |
| LNA 3 | catgTcaTgcggTTagg (SEQ ID 11) | 4 ± 1 | 22 | 5 |
| LNA 4 | catgTcaTgaCggTtagG (SEQ ID 11) | 5 ± 9 | 27 | 2 |
| LNA 5 | CaTgTcaTgaCggTTagG (SEQ ID 11) | 2 ± 3 | 44 | 2 |
| LNA 6 | catgTcatGacggTtagg (SEQ ID 11) | 12 ± 2 | 16 | 4 |
| LNA 7 | CatgTcatGacggTtagg (SEQ ID 11) | 8 ± 4 | 22 | 4 |
| LNA 8 | catgTcatGacggTtagG (SEQ ID 11) | 9 ± 1 | 22 | 4 |
| LNA 9 | CatgTcatGacggTtagG (SEQ ID 11) | 7 ± 2 | 27 | 4 |
| LNA 10 | CatgTcaTgaCggTtagG (SEQ ID 11) | 7 ± 1 | 33 | 2 |
| LNA 11 | CaTgTcatgacggTTagG (SEQ ID 11) | 81 ± 5 | 33 | 8 |
| | gaps | | | |
| LNA 12 | CatgTcaTgacggTtagG (SEQ ID 11) | 6 ± 4 | 27 | 5 |
| LNA 13 | CatgTcAtgacggTtagG (SEQ ID 11) | 49 ± 12 | 27 | 6 |
| LNA 14 | CatgTCatgacggTtagG (SEQ ID 11) | 83 ± 6 | 27 | 7 |
| LNA 15 | CatgTcatgacggTtagG (SEQ ID 11) | 91 ± 2 | 22 | 8 |
| | end block oligonucleotides | | | |
| LNA 16 | CATGTcatgacggTTAGG (SEQ ID 11) | 85 ± 6 | 55 | 8 |
| LNA 17 | CATGtcatgacggtTAGG (SEQ ID 11) | 94 ± 3 | 44 | 10 |
| LNA 18 | CATgtcatgacggttAGG (SEQ ID 11) | 93 ± 2 | 33 | 12 |
| LNA 19 | CatgtcatgacggttaGG (SEQ ID 11) | 87 ± 12 | 22 | 14 |
| LNA 20 | CatgtcatgacggttagG (SEQ ID 11) | 85 ± 6 | 11 | 16 |
| | control sequences | | | |
| DNA 2 | atcttgttgacggtctca (SEQ ID 39) | 97 ± 2 | 0 | — |

TABLE 3-continued

List of oligonucleotides used

| Name | Sequence | % mRNA cleavage | % LNA content | DNA gap |
|---|---|---|---|---|
| LNA 21 | A*tct*T*gtt*G*acgg*T*ctc*A (SEQ ID 39) | 0 ± 0 | 27 | 4 |
| LNA 22 | A*tct*T*gttgacgg*T*ctc*A (SEQ ID 39) | 95 ± 3 | 22 | 8 |
| LNA 23 | ATCTTgttgacggTCTCA (SEQ ID 39) | 97 ± 1 | 55 | 8 |

*Note: Lower case = DNA monomers; italic and underlined = phosphorothioates; bold characters = LNA monomers.

Various tests were carried out with these oligonucleotides:

a) Firstly, the percentage of RNA cleavage of VR1 by RNase H initiated by the oligonucleotide was investigated, the test conditions substantially matching those stated in Example 2.

The results are shown in Table 3. It was found that oligonucleotides with LNA only exhibited cleavage comparable with the native oligonucleotide if at least 6, or especially at least 8 contiguous nucleotides were not LNAs.

b) The melting temperature of the LNA/RNA:DNA hybrids were then measured by standard methods (Table 4). Surprisingly, the LNAs did not exhibit a raised melting temperature in comparison with the native oligonucleotides and the phosphorothioates. This is very favorable for stability.

TABLE 4

Melting temperature $T_m$ of LNA/DNA: RNA hybrids

| Oligonucleotide | No. of LNAs | $T_m$ ° C. |
|---|---|---|
| DNA1 | 0 | 58 |
| PS | 0 | 49 |
| LNA 20 | 2 | 61 |
| LNA 19 | 4 | 66 |
| LNA 18 | 6 | 73 |
| LNA 17 | 3 | 79 |
| LNA 16 | 10 | ~85 | c) The kinetics of RNase H cleavage were then investigated under identical conditions to those above, except that equimolar quantities of RNA and antisense oligonucleotide (100 nM each) were used. The results are shown in Table 5. Surprisingly, the oligonucleotide with LNA exhibited a distinct increase in activity in comparison with the native oligonucleotides and phosphorothioates.

TABLE 5

Rate constants for RNase H cleavage of "full-length" VR1 mRNA by antisense oligonucleotides.

| Oligonucleotide | k [min$^{-1}$] |
|---|---|
| DNA 1 | 0.17 ± 0.01 |
| LNA 17 | 1.1 ± 0.6 |
| PS | 0.07 ± 0.01 | d) Finally, the half-life of the radioactively labeled oligonucleotides with LNA of the native oligonucleotide and of the phosphorothioate was determined at 37° C. in human serum over a period of up to 2 days. The results are shown in Table 6. While the half-life of the native DNA is 1.5 h and that of the phosphorothioate is 10 h, the half-life of nucleotides with LNA, on the 3 or 4 ends, were significantly long with a $t_{1/2}$ of approximately 17 h.

TABLE 6

Half-life of native, phosphorothioate and end block LNA/DNA oligonucleotides in human serum.

| Oligonucleotide | nt end block | $t_{1/2}$ [h] |
|---|---|---|
| DNA 1 | 0 | 1.5 ± 0.3 |
| PS | 0 | 10 ± 2 |
| LNA 20 | 1 | 4 ± 2 |
| LNA 19 | 2 | 6 ± #?# |
| LNA 18 | 3 | 17 + 2 |
| LNA 17 | 4 | 15 ± 1 |
| LNA 16 | 5 | 15 + 2 |

The best restriction properties were thus achieved by the nucleotides with LNAs which had approximately 8 contiguous nucleotides without LNAs and had 3 or 4 LNAs on the 3' and 5' ends.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

BIBLIOGRAPHIC REFERENCES

Caterina, M. J.; Schumacher, M. A.; Tominaga, T. A.; Rosen, T. A.; Levine, J. D.; Julius, D. (1997) The capsaicin receptor: a heat-activated ion channel in the pain pathway. Nature 389, 816-824.

Caterina, M. J.; Leffler, A.; Malmberg, A. B.; Martin, W. J.; Trafton, J.; Petersen-Zeitz, K. R.; Koltzenburg, M; Basbaum, A. L; Julius, D. (2000) Impaired nociception and pain Sensation in mice lacking the capsaicin receptor. Science 288, 306-313.

Davis, J. B.; Gray, J.; Gunthorpe, M. J.; Hatcher, J. P.; Davey, P. T.; Overend, P.; Harries, M. H.; Latcham, J.; Clapham, C.; Atkinson, K.; Hughes, S. A.; Rance, K.; Grau, E.; Harper, A. J.; Pugh, P. L.; Rogers, D. C.; Bingham, S.; Randall, A.; Sheardown, S. A. (2000) Vanilloid receptor-1 is essential for inflammatory thermal hyperalgesia. Nature 405, 183-187.

Kim, S. H.; Chung, J. M. (1992) An experimental model for peripheral mononeuropathy produced by segmental spinal nerve ligation in the rat. Pain 50, 355-363.

Pogatzki, E. M.; Zahn, P. K.; Brennan, T. J. (2000) Lumbar catheterization of the subarachnoid space with a 32-gauge polyurethane catheter in the rat. Eur. J. Pain 4, 111-113.

Porreca, F.; Lai, J.; Bian, D.; Wegert, S.; Ossipov, M. H.; Eglen, R. M.; Kassotakis, L.; Novakovic, S.; Rabert, D. K.; Sangameswaran, L.; Hunter, J. C. (1999) A comparison of the potential role of the tetrodotoxin-insensitive sodium channels, PN3/SNS and NaN/SNS2, in rat models of chronic pain. Proc. Natl. Acad. Sei. USA 96, 7640-7644.

Santoro, S. W.; Joyce, G. F. (1997) A general purpose RNA-cleaving DNA enzyme. Proc. Natl. Acad. Sci. USA 94, 4262-4266.

Vaish, N.K. et al. (1998), Nucl. Acid Res. 26, 5237-5242.

What is claimed is:

1. An anti-sense oligonucleotide 15 to 30 nucleotides in length and comprising the sequence according to one of SEQ ID NOs 2-10, wherein each of SEQ ID NOs 2-10 comprises the sequence according to SEQ ID NO 1.

2. An oligonucleotide according to claim 1, comprising
   (1) the sequence according to SEQ ID NO 11, or
   (2) a sequence differing from (1) by at most two different bases not located in the sequence according to SEQ ID NO 1.

3. An anti-sense oligonucleotide 15 to 30 nucleotides in length and comprising
   (1) the sequence according to one of SEQ ID NOs 2-10, or
   (2) a sequence differing from (1) by one different base not located in the sequence according to SEQ ID NO 1.

4. An anti-sense oligonucleotide consisting of the sequence according to SEQ ID NO 11.

5. An oligonucleotide according to claim 1, wherein the length is 15 to 25 nucleotides.

6. An oligonucleotide according to claim 5, wherein the length is 17 to 19 nucleotides.

7. An oligonucleotide according to claim 6, wherein the length is 18 nucleotides.

8. An anti-sense oligonucleotide selected from the group consisting of SEQ ID NOs 1-11.

9. An oligonucleotide according to claim 1, comprising at least one modified ribose, at least one modified phosphodiester bond, or at least one modified base.

10. An oligonucleotide according to claim 1, wherein at least one of the nucleotides is a "locked nucleic acid" (LNA).

11. An oligonucleotide according to claim 1, wherein at least one of the nucleotides is a phosphorothioate.

12. An oligonucleotide according to claim 11, wherein at least one of the nucleotides is a "locked nucleic acid" (LNA).

13. An oligonucleotide according to claim 10, wherein LNAs are located at the 5' and 3' end of the oligonucleotide.

14. An oligonucleotide according to claim 13, wherein the terminal 2-5 nucleotides on the 3' and 5' end of the oligonucleotide are LNAs.

15. An oligonucleotide according to claim 14, wherein the terminal 3 or 4 nucleotides at the 3' and 5' ends are LNAs.

16. An oligonucleotide according to claim 10, wherein more than 6 contiguous nucleotides in the oligonucleotide are not LNAs.

17. An oligonucleotide according to claim 16, wherein more than 8 contiguous nucleotides in the oligonucleotide are not LNAs.

18. An oligonucleotide according to claim 16, wherein the more than 6 contiguous nucleotides that are not LNAs are in the sequence according to SEQ ID NO 1.

19. A polynucleotide construct coding for an oligonucleotide according to claim 1.

20. A ribozyme comprising an oligonucleotide of claim 1.

21. A ribozyme according to claim 20, which is a hammerhead ribozyme.

22. A DNA enzyme comprising an oligonucleotide of claim 1.

23. A DNA enzyme according to claim 22, which is a type 10-23 or 12-32 DNA enzyme.

24. A vector comprising a heterologous sequence which consists of an oligonucleotide of claim 1.

25. A vector according to claim 24, which is an expression vector.

26. A peptide nucleic acid (PNA) comprising an oligonucleotide of claim 1.

27. An oligonucleotide according to claim 1, bound to a protein, or packaged in a liposome.

28. An oligonucleotide according to claim 27, wherein the protein is tet-, transportin or ferritin.

29. An isolated cell comprising an oligonucleotide according to claim 1.

30. A pharmaceutical composition comprising at least one oligonucleotide according to claim 1, and a pharmaceutically acceptable carrier.

31. A pharmaceutical composition comprising at least one polynucleotide construct according to claim 19, and a pharmaceutically acceptable carrier.

32. A composition of matter comprising a cell according to claim 29, and a pharmaceutically acceptable carrier.

* * * * *

UNITED STATES PATENT AND TRADEMARK OFFICE
CERTIFICATE OF CORRECTION

PATENT NO. : 7,662,948 B2 Page 1 of 1
APPLICATION NO. : 10/376341
DATED : February 16, 2010
INVENTOR(S) : Kurreck et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 939 days.

Signed and Sealed this

Twenty-eighth Day of December, 2010

David J. Kappos
*Director of the United States Patent and Trademark Office*

SEQUENCE LISTING

```
<160> NUMBER OF SEQ ID NOS: 251

<210> SEQ ID NO 1
<211> LENGTH: 9
<212> TYPE: DNA
<213> ORGANISM: Rattus norvegicus

<400> SEQUENCE: 1 catgacggt                                                                  9

<210> SEQ ID NO 2
<211> LENGTH: 15
<212> TYPE: DNA
<213> ORGANISM: Rattus norvegicus

<400> SEQUENCE: 2
gtcatgacgg ttagg                                                          15

<210> SEQ ID NO 3
<211> LENGTH: 15
<212> TYPE: DNA
<213> ORGANISM: Rattus norvegicus

<400> SEQUENCE: 3
tgtcatgacg gttag                                                          15
```

-continued

```
<210> SEQ ID NO 4
<211> LENGTH: 15
<212> TYPE: DNA
<213> ORGANISM: Rattus norvegicus

<400> SEQUENCE: 4
atgtcatgac ggtta                                                  15

<210> SEQ ID NO 5
<211> LENGTH: 15
<212> TYPE: DNA
<213> ORGANISM: Rattus norvegicus

<400> SEQUENCE: 5
catgtcatga cggtt                                                  15

<210> SEQ ID NO 6
<211> LENGTH: 16
<212> TYPE: DNA
<213> ORGANISM: Rattus norvegicus

<400> SEQUENCE: 6
tgtcatgacg gttagg                                                 16

<210> SEQ ID NO 7
<211> LENGTH: 16
<212> TYPE: DNA
<213> ORGANISM: Rattus norvegicus

<400> SEQUENCE: 7
atgtcatgac ggttag                                                 16

<210> SEQ ID NO 8
<211> LENGTH: 16
<212> TYPE: DNA
<213> ORGANISM: Rattus norvegicus

<400> SEQUENCE: 8
catgtcatga cggtta                                                 16

<210> SEQ ID NO 9
<211> LENGTH: 17
<212> TYPE: DNA
<213> ORGANISM: Rattus norvegicus

<400> SEQUENCE: 9
atgtcatgac ggttagg                                                17

<210> SEQ ID NO 10
<211> LENGTH: 17
<212> TYPE: DNA
<213> ORGANISM: Rattus norvegicus

<400> SEQUENCE: 10
catgtcatga cggttag                                                17

<210> SEQ ID NO 11
<211> LENGTH: 18
<212> TYPE: DNA
<213> ORGANISM: Rattus norvegicus

<400> SEQUENCE: 11
catgtcatga cggttagg                                               18
```

<210> SEQ ID NO 12
<211> LENGTH: 15
<212> TYPE: DNA
<213> ORGANISM: Rattus norvegicus
<220> FEATURE:
<221> NAME/KEY: misc_feature
<222> LOCATION: (8)..(8)
<223> OTHER INFORMATION: n can be any nucleotide

<400> SEQUENCE: 12
gtcatgangg ttagg                                                    15

<210> SEQ ID NO 13
<211> LENGTH: 17
<212> TYPE: DNA
<213> ORGANISM: Rattus norvegicus
<220> FEATURE:
<221> NAME/KEY: misc_feature
<222> LOCATION: (9)..(9)
<223> OTHER INFORMATION: n can be any nucleotide

<400> SEQUENCE: 13
tgtcatgang gttaggg                                                  17

<210> SEQ ID NO 14
<211> LENGTH: 19
<212> TYPE: DNA
<213> ORGANISM: Rattus norvegicus
<220> FEATURE:
<221> NAME/KEY: misc_feature
<222> LOCATION: (10)..(10)
<223> OTHER INFORMATION: n can be any nucleotide

<400> SEQUENCE: 14
atgtcatgan ggttagggg                                                19

<210> SEQ ID NO 15
<211> LENGTH: 15
<212> TYPE: RNA
<213> ORGANISM: Rattus norvegicus
<220> FEATURE:
<221> NAME/KEY: misc_feature
<222> LOCATION: (8)..(8)
<223> OTHER INFORMATION: n can be any nucleotide

<400> SEQUENCE: 15
augucaunac gguua                                                    15

<210> SEQ ID NO 16
<211> LENGTH: 17
<212> TYPE: RNA
<213> ORGANISM: Rattus norvegicus
<220> FEATURE:
<221> NAME/KEY: misc_feature
<222> LOCATION: (9)..(9)
<223> OTHER INFORMATION: n can be any nucleotide

<400> SEQUENCE: 16
caugucauna cgguuag                                                  17

<210> SEQ ID NO 17
<211> LENGTH: 19
<212> TYPE: RNA
<213> ORGANISM: Rattus norvegicus
<220> FEATURE:
<221> NAME/KEY: misc_feature
<222> LOCATION: (10)..(10)
<223> OTHER INFORMATION: n can be any nucleotide

<400> SEQUENCE: 17
gcaugucaun acgguuagg                                                   19

<210> SEQ ID NO 18
<211> LENGTH: 9
<212> TYPE: DNA
<213> ORGANISM: Rattus norvegicus

<400> SEQUENCE: 18 cgtggcgat                                                               9

<210> SEQ ID NO 19
<211> LENGTH: 15
<212> TYPE: DNA
<213> ORGANISM: Rattus norvegicus

<400> SEQUENCE: 19
gtcgtggcga ttagg                                                       15

<210> SEQ ID NO 20
<211> LENGTH: 15
<212> TYPE: DNA
<213> ORGANISM: Rattus norvegicus

<400> SEQUENCE: 20
tgtcgtggcg attag                                                       15

<210> SEQ ID NO 21
<211> LENGTH: 15
<212> TYPE: DNA
<213> ORGANISM: Rattus norvegicus

<400> SEQUENCE: 21
atgtcgtggc gatta                                                       15

<210> SEQ ID NO 22
<211> LENGTH: 15
<212> TYPE: DNA
<213> ORGANISM: Rattus norvegicus

<400> SEQUENCE: 22
catgtcgtgg cgatt                                                       15

<210> SEQ ID NO 23
<211> LENGTH: 16
<212> TYPE: DNA
<213> ORGANISM: Rattus norvegicus

<400> SEQUENCE: 23
tgtcgtggcg attagg                                                      16

<210> SEQ ID NO 24
<211> LENGTH: 16
<212> TYPE: DNA
<213> ORGANISM: Rattus norvegicus

<400> SEQUENCE: 24
atgtcgtggc gattag                                                      16

<210> SEQ ID NO 25
<211> LENGTH: 16
<212> TYPE: DNA

<210> SEQ ID NO 25
<211> LENGTH: 16
<212> TYPE: DNA
<213> ORGANISM: Rattus norvegicus

<400> SEQUENCE: 25
catgtcgtgg cgatta                                                   16

<210> SEQ ID NO 26
<211> LENGTH: 17
<212> TYPE: DNA
<213> ORGANISM: Rattus norvegicus

<400> SEQUENCE: 26
atgtcgtggc gattagg                                                  17

<210> SEQ ID NO 27
<211> LENGTH: 17
<212> TYPE: DNA
<213> ORGANISM: Rattus norvegicus

<400> SEQUENCE: 27
catgtcgtgg cgattag                                                  17

<210> SEQ ID NO 28
<211> LENGTH: 18
<212> TYPE: DNA
<213> ORGANISM: Rattus norvegicus

<400> SEQUENCE: 28
catgtcgtgg cgattagg                                                 18

<210> SEQ ID NO 29
<211> LENGTH: 9
<212> TYPE: DNA
<213> ORGANISM: Rattus norvegicus

<400> SEQUENCE: 29 gttgacggt                                                            9

<210> SEQ ID NO 30
<211> LENGTH: 15
<212> TYPE: DNA
<213> ORGANISM: Rattus norvegicus

<400> SEQUENCE: 30
ttgttgacgg tctca                                                    15

<210> SEQ ID NO 31
<211> LENGTH: 15
<212> TYPE: DNA
<213> ORGANISM: Rattus norvegicus

<400> SEQUENCE: 31
cttgttgacg gtctc                                                    15

<210> SEQ ID NO 32
<211> LENGTH: 15
<212> TYPE: DNA
<213> ORGANISM: Rattus norvegicus

<400> SEQUENCE: 32
tcttgttgac ggtct                                                    15

<210> SEQ ID NO 33
<211> LENGTH: 15

```
<212> TYPE: DNA
<213> ORGANISM: Rattus norvegicus

<400> SEQUENCE: 33
atcttgttga cggtc                                              15

<210> SEQ ID NO 34
<211> LENGTH: 16
<212> TYPE: DNA
<213> ORGANISM: Rattus norvegicus

<400> SEQUENCE: 34
cttgttgacg gtctca                                             16

<210> SEQ ID NO 35
<211> LENGTH: 16
<212> TYPE: DNA
<213> ORGANISM: Rattus norvegicus

<400> SEQUENCE: 35
tcttgttgac ggtctc                                             16

<210> SEQ ID NO 36
<211> LENGTH: 16
<212> TYPE: DNA
<213> ORGANISM: Rattus norvegicus

<400> SEQUENCE: 36
atcttgttga cggtct                                             16

<210> SEQ ID NO 37
<211> LENGTH: 17
<212> TYPE: DNA
<213> ORGANISM: Rattus norvegicus

<400> SEQUENCE: 37
tcttgttgac ggtctca                                            17

<210> SEQ ID NO 38
<211> LENGTH: 17
<212> TYPE: DNA
<213> ORGANISM: Rattus norvegicus

<400> SEQUENCE: 38
atcttgttga cggtctc                                            17

<210> SEQ ID NO 39
<211> LENGTH: 18
<212> TYPE: DNA
<213> ORGANISM: Rattus norvegicus

<400> SEQUENCE: 39
atcttgttga cggtctca                                           18

<210> SEQ ID NO 40
<211> LENGTH: 15
<212> TYPE: DNA
<213> ORGANISM: Rattus norvegicus
<220> FEATURE:
<221> NAME/KEY: misc_feature
<222> LOCATION: (8)..(8)
<223> OTHER INFORMATION: n can be any nucleotide

<400> SEQUENCE: 40
```
ttgttgangg tctca                                                    15

<210> SEQ ID NO 41
<211> LENGTH: 17
<212> TYPE: DNA
<213> ORGANISM: Rattus norvegicus
<220> FEATURE:
<221> NAME/KEY: misc_feature
<222> LOCATION: (9)..(9)
<223> OTHER INFORMATION: n can be any nucleotide

<400> SEQUENCE: 41
cttgttgang gtctcac                                                  17

<210> SEQ ID NO 42
<211> LENGTH: 19
<212> TYPE: DNA
<213> ORGANISM: Rattus norvegicus
<220> FEATURE:
<221> NAME/KEY: misc_feature
<222> LOCATION: (10)..(10)
<223> OTHER INFORMATION: n can be any nucleotide

<400> SEQUENCE: 42
tcttgttgan ggtctcacc                                                19

<210> SEQ ID NO 43
<211> LENGTH: 15
<212> TYPE: RNA
<213> ORGANISM: Rattus norvegicus
<220> FEATURE:
<221> NAME/KEY: misc_feature
<222> LOCATION: (8)..(8)
<223> OTHER INFORMATION: n can be any nucleotide

<400> SEQUENCE: 43
ucuuguunac ggucu                                                    15

<210> SEQ ID NO 44
<211> LENGTH: 17
<212> TYPE: RNA
<213> ORGANISM: Rattus norvegicus
<220> FEATURE:
<221> NAME/KEY: misc_feature
<222> LOCATION: (9)..(9)
<223> OTHER INFORMATION: n can be any nucleotide

<400> SEQUENCE: 44
aucuuguuna cggucuc                                                  17

<210> SEQ ID NO 45
<211> LENGTH: 19
<212> TYPE: RNA
<213> ORGANISM: Rattus norvegicus
<220> FEATURE:
<221> NAME/KEY: misc_feature
<222> LOCATION: (10)..(10)
<223> OTHER INFORMATION: n can be any nucleotide

<400> SEQUENCE: 45
aaucuuguun acggucuca                                                19

<210> SEQ ID NO 46
<211> LENGTH: 9
<212> TYPE: DNA
<213> ORGANISM: Rattus norvegicus

<400> SEQUENCE: 46

-continued gttgacagt					9

<210> SEQ ID NO 47
<211> LENGTH: 15
<212> TYPE: DNA
<213> ORGANISM: Rattus norvegicus

<400> SEQUENCE: 47
ttgttgacag tctca				15

<210> SEQ ID NO 48
<211> LENGTH: 15
<212> TYPE: DNA
<213> ORGANISM: Rattus norvegicus

<400> SEQUENCE: 48
cttgttgaca gtctc				15

<210> SEQ ID NO 49
<211> LENGTH: 15
<212> TYPE: DNA
<213> ORGANISM: Rattus norvegicus

<400> SEQUENCE: 49
tcttgttgac agtct				15

<210> SEQ ID NO 50
<211> LENGTH: 15
<212> TYPE: DNA
<213> ORGANISM: Rattus norvegicus

<400> SEQUENCE: 50
atcttgttga cagtc				15

<210> SEQ ID NO 51
<211> LENGTH: 16
<212> TYPE: DNA
<213> ORGANISM: Rattus norvegicus

<400> SEQUENCE: 51
cttgttgaca gtctca				16

<210> SEQ ID NO 52
<211> LENGTH: 16
<212> TYPE: DNA
<213> ORGANISM: Rattus norvegicus

<400> SEQUENCE: 52
tcttgttgac agtctc				16

<210> SEQ ID NO 53
<211> LENGTH: 16
<212> TYPE: DNA
<213> ORGANISM: Rattus norvegicus

<400> SEQUENCE: 53
atcttgttga cagtct				16

<210> SEQ ID NO 54
<211> LENGTH: 17
<212> TYPE: DNA
<213> ORGANISM: Rattus norvegicus

```
<400> SEQUENCE: 54
tcttgttgac agtctca                                                  17

<210> SEQ ID NO 55
<211> LENGTH: 17
<212> TYPE: DNA
<213> ORGANISM: Rattus norvegicus

<400> SEQUENCE: 55
atcttgttga cagtctc                                                  17

<210> SEQ ID NO 56
<211> LENGTH: 18
<212> TYPE: DNA
<213> ORGANISM: Rattus norvegicus

<400> SEQUENCE: 56
atcttgttga cagtctca                                                 18

<210> SEQ ID NO 57
<211> LENGTH: 15
<212> TYPE: DNA
<213> ORGANISM: Rattus norvegicus
<220> FEATURE:
<221> NAME/KEY: misc_feature
<222> LOCATION: (8)..(8)
<223> OTHER INFORMATION: n can be any nucleotide

<400> SEQUENCE: 57
ttgttganag tctca                                                    15

<210> SEQ ID NO 58
<211> LENGTH: 17
<212> TYPE: DNA
<213> ORGANISM: Rattus norvegicus
<220> FEATURE:
<221> NAME/KEY: misc_feature
<222> LOCATION: (9)..(9)
<223> OTHER INFORMATION: n can be any nucleotide
<220> FEATURE:
<221> NAME/KEY: misc_feature
<222> LOCATION: (17)..(17)
<223> OTHER INFORMATION: n can be any nucleotide

<400> SEQUENCE: 58
cttgttgana gtctcan                                                  17

<210> SEQ ID NO 59
<211> LENGTH: 19
<212> TYPE: DNA
<213> ORGANISM: Rattus norvegicus
<220> FEATURE:
<221> NAME/KEY: misc_feature
<222> LOCATION: (10)..(10)
<223> OTHER INFORMATION: n can be any nucleotide
<220> FEATURE:
<221> NAME/KEY: misc_feature
<222> LOCATION: (18)..(18)
<223> OTHER INFORMATION: n can be any nucleotide
<220> FEATURE:
<221> NAME/KEY: misc_feature
<222> LOCATION: (19)..(19)
<223> OTHER INFORMATION: n can be any nucleotide

<400> SEQUENCE: 59
tcttgttgan agtctcann                                                19
```

```
<210> SEQ ID NO 60
<211> LENGTH: 15
<212> TYPE: RNA
<213> ORGANISM: Rattus norvegicus
<220> FEATURE:
<221> NAME/KEY: misc_feature
<222> LOCATION: (8)..(8)
<223> OTHER INFORMATION: n can be any nucleotide

<400> SEQUENCE: 60
ucuuguunac agucu                                                    15

<210> SEQ ID NO 61
<211> LENGTH: 17
<212> TYPE: RNA
<213> ORGANISM: Rattus norvegicus
<220> FEATURE:
<221> NAME/KEY: misc_feature
<222> LOCATION: (9)..(9)
<223> OTHER INFORMATION: n can be any nucleotide

<400> SEQUENCE: 61
aucuuguuna cagucuc                                                  17

<210> SEQ ID NO 62
<211> LENGTH: 19
<212> TYPE: RNA
<213> ORGANISM: Rattus norvegicus
<220> FEATURE:
<221> NAME/KEY: misc_feature
<222> LOCATION: (1)..(1)
<223> OTHER INFORMATION: n can be any nucleotide
<220> FEATURE:
<221> NAME/KEY: misc_feature
<222> LOCATION: (10)..(10)
<223> OTHER INFORMATION: n can be any nucleotide

<400> SEQUENCE: 62
naucuuguun acagucuca                                                19

<210> SEQ ID NO 63
<211> LENGTH: 9
<212> TYPE: DNA
<213> ORGANISM: Rattus norvegicus

<400> SEQUENCE: 63 cctgacctc                                                            9

<210> SEQ ID NO 64
<211> LENGTH: 15
<212> TYPE: DNA
<213> ORGANISM: Rattus norvegicus

<400> SEQUENCE: 64
ggcctgacct caggg                                                    15

<210> SEQ ID NO 65
<211> LENGTH: 15
<212> TYPE: DNA
<213> ORGANISM: Rattus norvegicus

<400> SEQUENCE: 65
cggcctgacc tcagg                                                    15

<210> SEQ ID NO 66
<211> LENGTH: 15
<212> TYPE: DNA
```

<213> ORGANISM: Rattus norvegicus

<400> SEQUENCE: 66
tcggcctgac ctcag                                          15

<210> SEQ ID NO 67
<211> LENGTH: 15
<212> TYPE: DNA
<213> ORGANISM: Rattus norvegicus

<400> SEQUENCE: 67
ctcggcctga cctca                                          15

<210> SEQ ID NO 68
<211> LENGTH: 16
<212> TYPE: DNA
<213> ORGANISM: Rattus norvegicus

<400> SEQUENCE: 68
cggcctgacc tcaggg                                         16

<210> SEQ ID NO 69
<211> LENGTH: 16
<212> TYPE: DNA
<213> ORGANISM: Rattus norvegicus

<400> SEQUENCE: 69
tcggcctgac ctcagg                                         16

<210> SEQ ID NO 70
<211> LENGTH: 16
<212> TYPE: DNA
<213> ORGANISM: Rattus norvegicus

<400> SEQUENCE: 70
ctcggcctga cctcag                                         16

<210> SEQ ID NO 71
<211> LENGTH: 17
<212> TYPE: DNA
<213> ORGANISM: Rattus norvegicus

<400> SEQUENCE: 71
tcggcctgac ctcaggg                                        17

<210> SEQ ID NO 72
<211> LENGTH: 17
<212> TYPE: DNA
<213> ORGANISM: Rattus norvegicus

<400> SEQUENCE: 72
ctcggcctga cctcagg                                        17

<210> SEQ ID NO 73
<211> LENGTH: 18
<212> TYPE: DNA
<213> ORGANISM: Rattus norvegicus

<400> SEQUENCE: 73
ctcggcctga cctcaggg                                       18

<210> SEQ ID NO 74
<211> LENGTH: 15

```
<212> TYPE: DNA
<213> ORGANISM: Rattus norvegicus
<220> FEATURE:
<221> NAME/KEY: misc_feature
<222> LOCATION: (8)..(8)
<223> OTHER INFORMATION: n can be any nucleotide

<400> SEQUENCE: 74
ggcctganct caggg                                                    15

<210> SEQ ID NO 75
<211> LENGTH: 17
<212> TYPE: DNA
<213> ORGANISM: Rattus norvegicus
<220> FEATURE:
<221> NAME/KEY: misc_feature
<222> LOCATION: (9)..(9)
<223> OTHER INFORMATION: n can be any nucleotide

<400> SEQUENCE: 75
cggcctganc tcaggga                                                  17

<210> SEQ ID NO 76
<211> LENGTH: 19
<212> TYPE: DNA
<213> ORGANISM: Rattus norvegicus
<220> FEATURE:
<221> NAME/KEY: misc_feature
<222> LOCATION: (10)..(10)
<223> OTHER INFORMATION: n can be any nucleotide

<400> SEQUENCE: 76
tcggcctgan ctcagggag                                                19

<210> SEQ ID NO 77
<211> LENGTH: 15
<212> TYPE: RNA
<213> ORGANISM: Rattus norvegicus
<220> FEATURE:
<221> NAME/KEY: misc_feature
<222> LOCATION: (8)..(8)
<223> OTHER INFORMATION: n can be any nucleotide

<400> SEQUENCE: 77
ucggccunac cucag                                                    15

<210> SEQ ID NO 78
<211> LENGTH: 17
<212> TYPE: RNA
<213> ORGANISM: Rattus norvegicus
<220> FEATURE:
<221> NAME/KEY: misc_feature
<222> LOCATION: (9)..(9)
<223> OTHER INFORMATION: n can be any nucleotide

<400> SEQUENCE: 78
cucggccuna ccucagg                                                  17

<210> SEQ ID NO 79
<211> LENGTH: 19
<212> TYPE: RNA
<213> ORGANISM: Rattus norvegicus
<220> FEATURE:
<221> NAME/KEY: misc_feature
<222> LOCATION: (1)..(1)
<223> OTHER INFORMATION: n can be any nucleotide
<220> FEATURE:
<221> NAME/KEY: misc_feature
<222> LOCATION: (10)..(10)
```

<223> OTHER INFORMATION: n can be any nucleotide

<400> SEQUENCE: 79
ncucggccun accucaggg                                                19

<210> SEQ ID NO 80
<211> LENGTH: 9
<212> TYPE: DNA
<213> ORGANISM: Rattus norvegicus

<400> SEQUENCE: 80 cttgaccgc                                                           9

<210> SEQ ID NO 81
<211> LENGTH: 15
<212> TYPE: DNA
<213> ORGANISM: Rattus norvegicus

<400> SEQUENCE: 81
tgcttgaccg caggg                                                   15

<210> SEQ ID NO 82
<211> LENGTH: 15
<212> TYPE: DNA
<213> ORGANISM: Rattus norvegicus

<400> SEQUENCE: 82
ctgcttgacc gcagg                                                   15

<210> SEQ ID NO 83
<211> LENGTH: 15
<212> TYPE: DNA
<213> ORGANISM: Rattus norvegicus

<400> SEQUENCE: 83
tctgcttgac cgcag                                                   15

<210> SEQ ID NO 84
<211> LENGTH: 15
<212> TYPE: DNA
<213> ORGANISM: Rattus norvegicus

<400> SEQUENCE: 84
ctctgcttga ccgca                                                   15

<210> SEQ ID NO 85
<211> LENGTH: 16
<212> TYPE: DNA
<213> ORGANISM: Rattus norvegicus

<400> SEQUENCE: 85
ctgcttgacc gcaggg                                                  16

<210> SEQ ID NO 86
<211> LENGTH: 16
<212> TYPE: DNA
<213> ORGANISM: Rattus norvegicus

<400> SEQUENCE: 86
tctgcttgac cgcagg                                                  16

<210> SEQ ID NO 87
<211> LENGTH: 16

```
<212> TYPE: DNA
<213> ORGANISM: Rattus norvegicus

<400> SEQUENCE: 87
ctctgcttga ccgcag                                                    16

<210> SEQ ID NO 88
<211> LENGTH: 17
<212> TYPE: DNA
<213> ORGANISM: Rattus norvegicus

<400> SEQUENCE: 88
tctgcttgac cgcaggg                                                   17

<210> SEQ ID NO 89
<211> LENGTH: 17
<212> TYPE: DNA
<213> ORGANISM: Rattus norvegicus

<400> SEQUENCE: 89
ctctgcttga ccgcagg                                                   17

<210> SEQ ID NO 90
<211> LENGTH: 18
<212> TYPE: DNA
<213> ORGANISM: Rattus norvegicus

<400> SEQUENCE: 90
ctctgcttga ccgcaggg                                                  18

<210> SEQ ID NO 91
<211> LENGTH: 15
<212> TYPE: DNA
<213> ORGANISM: Rattus norvegicus
<220> FEATURE:
<221> NAME/KEY: misc_feature
<222> LOCATION: (8)..(8)
<223> OTHER INFORMATION: n can be any nucleotide

<400> SEQUENCE: 91
tgcttgancg caggg                                                     15

<210> SEQ ID NO 92
<211> LENGTH: 17
<212> TYPE: DNA
<213> ORGANISM: Rattus norvegicus
<220> FEATURE:
<221> NAME/KEY: misc_feature
<222> LOCATION: (9)..(9)
<223> OTHER INFORMATION: n can be any nucleotide
<220> FEATURE:
<221> NAME/KEY: misc_feature
<222> LOCATION: (17)..(17)
<223> OTHER INFORMATION: n can be any nucleotide

<400> SEQUENCE: 92
ctgcttganc gcagggn                                                   17

<210> SEQ ID NO 93
<211> LENGTH: 19
<212> TYPE: DNA
<213> ORGANISM: Rattus norvegicus
<220> FEATURE:
<221> NAME/KEY: misc_feature
<222> LOCATION: (10)..(10)
<223> OTHER INFORMATION: n can be any nucleotide
<220> FEATURE:
```

```
<221> NAME/KEY: misc_feature
<222> LOCATION: (18)..(18)
<223> OTHER INFORMATION: n can be any nucleotide
<220> FEATURE:
<221> NAME/KEY: misc_feature
<222> LOCATION: (19)..(19)
<223> OTHER INFORMATION: n can be any nucleotide

<400> SEQUENCE: 93
tctgcttgan cgcagggnn                                                    19

<210> SEQ ID NO 94
<211> LENGTH: 15
<212> TYPE: RNA
<213> ORGANISM: Rattus norvegicus
<220> FEATURE:
<221> NAME/KEY: misc_feature
<222> LOCATION: (8)..(8)
<223> OTHER INFORMATION: n can be any nucleotide

<400> SEQUENCE: 94
ucugcuunac cgcag                                                        15

<210> SEQ ID NO 95
<211> LENGTH: 17
<212> TYPE: RNA
<213> ORGANISM: Rattus norvegicus
<220> FEATURE:
<221> NAME/KEY: misc_feature
<222> LOCATION: (9)..(9)
<223> OTHER INFORMATION: n can be any nucleotide

<400> SEQUENCE: 95
cucugcuuna ccgcagg                                                      17

<210> SEQ ID NO 96
<211> LENGTH: 19
<212> TYPE: RNA
<213> ORGANISM: Rattus norvegicus
<220> FEATURE:
<221> NAME/KEY: misc_feature
<222> LOCATION: (1)..(1)
<223> OTHER INFORMATION: n can be any nucleotide
<220> FEATURE:
<221> NAME/KEY: misc_feature
<222> LOCATION: (10)..(10)
<223> OTHER INFORMATION: n can be any nucleotide

<400> SEQUENCE: 96
ncucugcuun accgcaggg                                                    19

<210> SEQ ID NO 97
<211> LENGTH: 9
<212> TYPE: DNA
<213> ORGANISM: Rattus norvegicus

<400> SEQUENCE: 97 gtggactcc                                                                9

<210> SEQ ID NO 98
<211> LENGTH: 15
<212> TYPE: DNA
<213> ORGANISM: Rattus norvegicus

<400> SEQUENCE: 98
gtgtggactc catag                                                        15
```

```
<210> SEQ ID NO 99
<211> LENGTH: 15
<212> TYPE: DNA
<213> ORGANISM: Rattus norvegicus

<400> SEQUENCE: 99
ggtgtggact ccata                                                    15

<210> SEQ ID NO 100
<211> LENGTH: 15
<212> TYPE: DNA
<213> ORGANISM: Rattus norvegicus

<400> SEQUENCE: 100
tggtgtggac tccat                                                    15

<210> SEQ ID NO 101
<211> LENGTH: 15
<212> TYPE: DNA
<213> ORGANISM: Rattus norvegicus

<400> SEQUENCE: 101
gtggtgtgga ctcca                                                    15

<210> SEQ ID NO 102
<211> LENGTH: 16
<212> TYPE: DNA
<213> ORGANISM: Rattus norvegicus

<400> SEQUENCE: 102
ggtgtggact ccatag                                                   16

<210> SEQ ID NO 103
<211> LENGTH: 16
<212> TYPE: DNA
<213> ORGANISM: Rattus norvegicus

<400> SEQUENCE: 103
tggtgtggac tccata                                                   16

<210> SEQ ID NO 104
<211> LENGTH: 16
<212> TYPE: DNA
<213> ORGANISM: Rattus norvegicus

<400> SEQUENCE: 104
gtggtgtgga ctccat                                                   16

<210> SEQ ID NO 105
<211> LENGTH: 17
<212> TYPE: DNA
<213> ORGANISM: Rattus norvegicus

<400> SEQUENCE: 105
tggtgtggac tccatag                                                  17

<210> SEQ ID NO 106
<211> LENGTH: 17
<212> TYPE: DNA
<213> ORGANISM: Rattus norvegicus

<400> SEQUENCE: 106
gtggtgtgga ctccata                                                  17
```

```
<210> SEQ ID NO 107
<211> LENGTH: 18
<212> TYPE: DNA
<213> ORGANISM: Rattus norvegicus

<400> SEQUENCE: 107
gtggtgtgga ctccatag                                                 18

<210> SEQ ID NO 108
<211> LENGTH: 15
<212> TYPE: DNA
<213> ORGANISM: Rattus norvegicus
<220> FEATURE:
<221> NAME/KEY: misc_feature
<222> LOCATION: (8)..(8)
<223> OTHER INFORMATION: n can be any nucleotide

<400> SEQUENCE: 108
gtgtggantc catag                                                    15

<210> SEQ ID NO 109
<211> LENGTH: 17
<212> TYPE: DNA
<213> ORGANISM: Rattus norvegicus
<220> FEATURE:
<221> NAME/KEY: misc_feature
<222> LOCATION: (9)..(9)
<223> OTHER INFORMATION: n can be any nucleotide

<400> SEQUENCE: 109
ggtgtggant ccatagg                                                  17

<210> SEQ ID NO 110
<211> LENGTH: 19
<212> TYPE: DNA
<213> ORGANISM: Rattus norvegicus
<220> FEATURE:
<221> NAME/KEY: misc_feature
<222> LOCATION: (10)..(10)
<223> OTHER INFORMATION: n can be any nucleotide

<400> SEQUENCE: 110
tggtgtggan tccataggc                                                19

<210> SEQ ID NO 111
<211> LENGTH: 15
<212> TYPE: RNA
<213> ORGANISM: Rattus norvegicus
<220> FEATURE:
<221> NAME/KEY: misc_feature
<222> LOCATION: (8)..(8)
<223> OTHER INFORMATION: n can be any nucleotide

<400> SEQUENCE: 111
uggugugnac uccau                                                    15

<210> SEQ ID NO 112
<211> LENGTH: 17
<212> TYPE: RNA
<213> ORGANISM: Rattus norvegicus
<220> FEATURE:
<221> NAME/KEY: misc_feature
<222> LOCATION: (9)..(9)
<223> OTHER INFORMATION: n can be any nucleotide

<400> SEQUENCE: 112
guggugugna cuccaua                                                  17
```

```
<210> SEQ ID NO 113
<211> LENGTH: 19
<212> TYPE: RNA
<213> ORGANISM: Rattus norvegicus
<220> FEATURE:
<221> NAME/KEY: misc_feature
<222> LOCATION: (1)..(1)
<223> OTHER INFORMATION: n can be any nucleotide
<220> FEATURE:
<221> NAME/KEY: misc_feature
<222> LOCATION: (10)..(10)
<223> OTHER INFORMATION: n can be any nucleotide

<400> SEQUENCE: 113
nguggugugn acuccauag                                              19

<210> SEQ ID NO 114
<211> LENGTH: 9
<212> TYPE: DNA
<213> ORGANISM: Rattus norvegicus

<400> SEQUENCE: 114 gtggactca                                                          9

<210> SEQ ID NO 115
<211> LENGTH: 15
<212> TYPE: DNA
<213> ORGANISM: Rattus norvegicus

<400> SEQUENCE: 115
acgtggactc agacg                                                  15

<210> SEQ ID NO 116
<211> LENGTH: 15
<212> TYPE: DNA
<213> ORGANISM: Rattus norvegicus

<400> SEQUENCE: 116
gacgtggact cagac                                                  15

<210> SEQ ID NO 117
<211> LENGTH: 15
<212> TYPE: DNA
<213> ORGANISM: Rattus norvegicus

<400> SEQUENCE: 117
cgacgtggac tcaga                                                  15

<210> SEQ ID NO 118
<211> LENGTH: 15
<212> TYPE: DNA
<213> ORGANISM: Rattus norvegicus

<400> SEQUENCE: 118
gcgacgtgga ctcag                                                  15

<210> SEQ ID NO 119
<211> LENGTH: 16
<212> TYPE: DNA
<213> ORGANISM: Rattus norvegicus

<400> SEQUENCE: 119
gacgtggact cagacg                                                 16
```

```
<210> SEQ ID NO 120
<211> LENGTH: 16
<212> TYPE: DNA
<213> ORGANISM: Rattus norvegicus

<400> SEQUENCE: 120
cgacgtggac tcagac                                                     16

<210> SEQ ID NO 121
<211> LENGTH: 16
<212> TYPE: DNA
<213> ORGANISM: Rattus norvegicus

<400> SEQUENCE: 121
gcgacgtgga ctcaga                                                     16

<210> SEQ ID NO 122
<211> LENGTH: 17
<212> TYPE: DNA
<213> ORGANISM: Rattus norvegicus

<400> SEQUENCE: 122
cgacgtggac tcagacg                                                    17

<210> SEQ ID NO 123
<211> LENGTH: 17
<212> TYPE: DNA
<213> ORGANISM: Rattus norvegicus

<400> SEQUENCE: 123
gcgacgtgga ctcagac                                                    17

<210> SEQ ID NO 124
<211> LENGTH: 18
<212> TYPE: DNA
<213> ORGANISM: Rattus norvegicus

<400> SEQUENCE: 124
gcgacgtgga ctcagacg                                                   18

<210> SEQ ID NO 125
<211> LENGTH: 15
<212> TYPE: DNA
<213> ORGANISM: Rattus norvegicus
<220> FEATURE:
<221> NAME/KEY: misc_feature
<222> LOCATION: (8)..(8)
<223> OTHER INFORMATION: n can be any nucleotide

<400> SEQUENCE: 125
acgtggantc agacg                                                      15

<210> SEQ ID NO 126
<211> LENGTH: 17
<212> TYPE: DNA
<213> ORGANISM: Rattus norvegicus
<220> FEATURE:
<221> NAME/KEY: misc_feature
<222> LOCATION: (9)..(9)
<223> OTHER INFORMATION: n can be any nucleotide
<220> FEATURE:
<221> NAME/KEY: misc_feature
<222> LOCATION: (17)..(17)
<223> OTHER INFORMATION: n can be any nucleotide

<400> SEQUENCE: 126
```

```
gacgtggant cagacgn                                               17
```

<210> SEQ ID NO 127
<211> LENGTH: 19
<212> TYPE: DNA
<213> ORGANISM: Rattus norvegicus
<220> FEATURE:
<221> NAME/KEY: misc_feature
<222> LOCATION: (10)..(10)
<223> OTHER INFORMATION: n can be any nucleotide
<220> FEATURE:
<221> NAME/KEY: misc_feature
<222> LOCATION: (18)..(18)
<223> OTHER INFORMATION: n can be any nucleotide
<220> FEATURE:
<221> NAME/KEY: misc_feature
<222> LOCATION: (19)..(19)
<223> OTHER INFORMATION: n can be any nucleotide

<400> SEQUENCE: 127

```
cgacgtggan tcagacgnn                                             19
```

<210> SEQ ID NO 128
<211> LENGTH: 15
<212> TYPE: RNA
<213> ORGANISM: Rattus norvegicus
<220> FEATURE:
<221> NAME/KEY: misc_feature
<222> LOCATION: (8)..(8)
<223> OTHER INFORMATION: n can be any nucleotide

<400> SEQUENCE: 128

```
cgacgugnac ucaga                                                 15
```

<210> SEQ ID NO 129
<211> LENGTH: 17
<212> TYPE: RNA
<213> ORGANISM: Rattus norvegicus
<220> FEATURE:
<221> NAME/KEY: misc_feature
<222> LOCATION: (9)..(9)
<223> OTHER INFORMATION: n can be any nucleotide

<400> SEQUENCE: 129

```
gcgacgugna cucagac                                               17
```

<210> SEQ ID NO 130
<211> LENGTH: 19
<212> TYPE: RNA
<213> ORGANISM: Rattus norvegicus
<220> FEATURE:
<221> NAME/KEY: misc_feature
<222> LOCATION: (1)..(1)
<223> OTHER INFORMATION: n can be any nucleotide
<220> FEATURE:
<221> NAME/KEY: misc_feature
<222> LOCATION: (10)..(10)
<223> OTHER INFORMATION: n can be any nucleotide

<400> SEQUENCE: 130

```
ngcgacgugn acucagacg                                             19
```

<210> SEQ ID NO 131
<211> LENGTH: 9
<212> TYPE: DNA
<213> ORGANISM: Rattus norvegicus

<400> SEQUENCE: 131

```
ggggactca                                                              9

<210> SEQ ID NO 132
<211> LENGTH: 15
<212> TYPE: DNA
<213> ORGANISM: Rattus norvegicus

<400> SEQUENCE: 132
gtggggactc agact                                                       15

<210> SEQ ID NO 133
<211> LENGTH: 15
<212> TYPE: DNA
<213> ORGANISM: Rattus norvegicus

<400> SEQUENCE: 133
ggtggggact cagac                                                       15

<210> SEQ ID NO 134
<211> LENGTH: 15
<212> TYPE: DNA
<213> ORGANISM: Rattus norvegicus

<400> SEQUENCE: 134
gggtggggac tcaga                                                       15

<210> SEQ ID NO 135
<211> LENGTH: 15
<212> TYPE: DNA
<213> ORGANISM: Rattus norvegicus

<400> SEQUENCE: 135
ggggtgggga ctcag                                                       15

<210> SEQ ID NO 136
<211> LENGTH: 16
<212> TYPE: DNA
<213> ORGANISM: Rattus norvegicus

<400> SEQUENCE: 136
ggtggggact cagact                                                      16

<210> SEQ ID NO 137
<211> LENGTH: 16
<212> TYPE: DNA
<213> ORGANISM: Rattus norvegicus

<400> SEQUENCE: 137
gggtggggac tcagac                                                      16

<210> SEQ ID NO 138
<211> LENGTH: 16
<212> TYPE: DNA
<213> ORGANISM: Rattus norvegicus

<400> SEQUENCE: 138
ggggtgggga ctcaga                                                      16

<210> SEQ ID NO 139
<211> LENGTH: 17
<212> TYPE: DNA
<213> ORGANISM: Rattus norvegicus

<400> SEQUENCE: 139
```
gggtggggac tcagact                                                17

<210> SEQ ID NO 140
<211> LENGTH: 17
<212> TYPE: DNA
<213> ORGANISM: Rattus norvegicus

<400> SEQUENCE: 140
ggggtgggga ctcagac                                                17

<210> SEQ ID NO 141
<211> LENGTH: 18
<212> TYPE: DNA
<213> ORGANISM: Rattus norvegicus

<400> SEQUENCE: 141
ggggtgggga ctcagact                                               18

<210> SEQ ID NO 142
<211> LENGTH: 15
<212> TYPE: DNA
<213> ORGANISM: Rattus norvegicus
<220> FEATURE:
<221> NAME/KEY: misc_feature
<222> LOCATION: (8)..(8)
<223> OTHER INFORMATION: n can be any nucleotide

<400> SEQUENCE: 142 gtgggganatc agact                                                 15

<210> SEQ ID NO 143
<211> LENGTH: 17
<212> TYPE: DNA
<213> ORGANISM: Rattus norvegicus
<220> FEATURE:
<221> NAME/KEY: misc_feature
<222> LOCATION: (9)..(9)
<223> OTHER INFORMATION: n can be any nucleotide

<400> SEQUENCE: 143
ggtggggant cagactc                                                17

<210> SEQ ID NO 144
<211> LENGTH: 19
<212> TYPE: DNA
<213> ORGANISM: Rattus norvegicus
<220> FEATURE:
<221> NAME/KEY: misc_feature
<222> LOCATION: (10)..(10)
<223> OTHER INFORMATION: n can be any nucleotide

<400> SEQUENCE: 144
gggtggggan tcagactcc                                              19

<210> SEQ ID NO 145
<211> LENGTH: 15
<212> TYPE: RNA
<213> ORGANISM: Rattus norvegicus
<220> FEATURE:
<221> NAME/KEY: misc_feature
<222> LOCATION: (8)..(8)
<223> OTHER INFORMATION: n can be any nucleotide

<400> SEQUENCE: 145 ggguggggnac ucaga                                                 15

```
<210> SEQ ID NO 146
<211> LENGTH: 17
<212> TYPE: RNA
<213> ORGANISM: Rattus norvegicus
<220> FEATURE:
<221> NAME/KEY: misc_feature
<222> LOCATION: (9)..(9)
<223> OTHER INFORMATION: n can be any nucleotide

<400> SEQUENCE: 146
ggggugggna cucagac                                                  17

<210> SEQ ID NO 147
<211> LENGTH: 19
<212> TYPE: RNA
<213> ORGANISM: Rattus norvegicus
<220> FEATURE:
<221> NAME/KEY: misc_feature
<222> LOCATION: (1)..(1)
<223> OTHER INFORMATION: n can be any nucleotide
<220> FEATURE:
<221> NAME/KEY: misc_feature
<222> LOCATION: (10)..(10)
<223> OTHER INFORMATION: n can be any nucleotide

<400> SEQUENCE: 147 ngggguggt acucagacu                                                 19

<210> SEQ ID NO 148
<211> LENGTH: 9
<212> TYPE: DNA
<213> ORGANISM: Rattus norvegicus

<400> SEQUENCE: 148 gggtccgca                                                            9

<210> SEQ ID NO 149
<211> LENGTH: 15
<212> TYPE: DNA
<213> ORGANISM: Rattus norvegicus

<400> SEQUENCE: 149
gtgggtccgc agcag                                                    15

<210> SEQ ID NO 150
<211> LENGTH: 15
<212> TYPE: DNA
<213> ORGANISM: Rattus norvegicus

<400> SEQUENCE: 150
agtgggtccg cagca                                                    15

<210> SEQ ID NO 151
<211> LENGTH: 15
<212> TYPE: DNA
<213> ORGANISM: Rattus norvegicus

<400> SEQUENCE: 151
gagtgggtcc gcagc                                                    15

<210> SEQ ID NO 152
<211> LENGTH: 15
<212> TYPE: DNA
<213> ORGANISM: Rattus norvegicus

<400> SEQUENCE: 152
```

```
ggagtgggtc cgcag                                                      15

<210> SEQ ID NO 153
<211> LENGTH: 16
<212> TYPE: DNA
<213> ORGANISM: Rattus norvegicus

<400> SEQUENCE: 153
agtgggtccg cagcag                                                     16

<210> SEQ ID NO 154
<211> LENGTH: 16
<212> TYPE: DNA
<213> ORGANISM: Rattus norvegicus

<400> SEQUENCE: 154
gagtgggtcc gcagca                                                     16

<210> SEQ ID NO 155
<211> LENGTH: 16
<212> TYPE: DNA
<213> ORGANISM: Rattus norvegicus

<400> SEQUENCE: 155
ggagtgggtc cgcagc                                                     16

<210> SEQ ID NO 156
<211> LENGTH: 17
<212> TYPE: DNA
<213> ORGANISM: Rattus norvegicus

<400> SEQUENCE: 156
gagtgggtcc gcagcag                                                    17

<210> SEQ ID NO 157
<211> LENGTH: 17
<212> TYPE: DNA
<213> ORGANISM: Rattus norvegicus

<400> SEQUENCE: 157
ggagtgggtc cgcagca                                                    17

<210> SEQ ID NO 158
<211> LENGTH: 18
<212> TYPE: DNA
<213> ORGANISM: Rattus norvegicus

<400> SEQUENCE: 158
ggagtgggtc cgcagcag                                                   18

<210> SEQ ID NO 159
<211> LENGTH: 9
<212> TYPE: DNA
<213> ORGANISM: Rattus norvegicus

<400> SEQUENCE: 159 cttgacaaa                                                             9

<210> SEQ ID NO 160
<211> LENGTH: 15
<212> TYPE: DNA
<213> ORGANISM: Rattus norvegicus
```

```
<400> SEQUENCE: 160
cgcttgacaa atctg                                                    15

<210> SEQ ID NO 161
<211> LENGTH: 15
<212> TYPE: DNA
<213> ORGANISM: Rattus norvegicus

<400> SEQUENCE: 161
gcgcttgaca aatct                                                    15

<210> SEQ ID NO 162
<211> LENGTH: 15
<212> TYPE: DNA
<213> ORGANISM: Rattus norvegicus

<400> SEQUENCE: 162
tgcgcttgac aaatc                                                    15

<210> SEQ ID NO 163
<211> LENGTH: 15
<212> TYPE: DNA
<213> ORGANISM: Rattus norvegicus

<400> SEQUENCE: 163
atgcgcttga caaat                                                    15

<210> SEQ ID NO 164
<211> LENGTH: 16
<212> TYPE: DNA
<213> ORGANISM: Rattus norvegicus

<400> SEQUENCE: 164
gcgcttgaca aatctg                                                   16

<210> SEQ ID NO 165
<211> LENGTH: 16
<212> TYPE: DNA
<213> ORGANISM: Rattus norvegicus

<400> SEQUENCE: 165
tgcgcttgac aaatct                                                   16

<210> SEQ ID NO 166
<211> LENGTH: 16
<212> TYPE: DNA
<213> ORGANISM: Rattus norvegicus

<400> SEQUENCE: 166
atgcgcttga caaatc                                                   16

<210> SEQ ID NO 167
<211> LENGTH: 17
<212> TYPE: DNA
<213> ORGANISM: Rattus norvegicus

<400> SEQUENCE: 167
tgcgcttgac aaatctg                                                  17

<210> SEQ ID NO 168
<211> LENGTH: 17
<212> TYPE: DNA
<213> ORGANISM: Rattus norvegicus
```

```
<400> SEQUENCE: 168
atgcgcttga caaatct                                                    17

<210> SEQ ID NO 169
<211> LENGTH: 18
<212> TYPE: DNA
<213> ORGANISM: Rattus norvegicus

<400> SEQUENCE: 169
atgcgcttga caaatctg                                                   18

<210> SEQ ID NO 170
<211> LENGTH: 15
<212> TYPE: DNA
<213> ORGANISM: Rattus norvegicus
<220> FEATURE:
<221> NAME/KEY: misc_feature
<222> LOCATION: (8)..(8)
<223> OTHER INFORMATION: n can be any nucleotide

<400> SEQUENCE: 170
cgcttganaa atctg                                                      15

<210> SEQ ID NO 171
<211> LENGTH: 17
<212> TYPE: DNA
<213> ORGANISM: Rattus norvegicus
<220> FEATURE:
<221> NAME/KEY: misc_feature
<222> LOCATION: (9)..(9)
<223> OTHER INFORMATION: n can be any nucleotide

<400> SEQUENCE: 171
gcgcttgana aatctgt                                                    17

<210> SEQ ID NO 172
<211> LENGTH: 19
<212> TYPE: DNA
<213> ORGANISM: Rattus norvegicus
<220> FEATURE:
<221> NAME/KEY: misc_feature
<222> LOCATION: (10)..(10)
<223> OTHER INFORMATION: n can be any nucleotide

<400> SEQUENCE: 172
tgcgcttgan aaatctgtc                                                  19

<210> SEQ ID NO 173
<211> LENGTH: 15
<212> TYPE: RNA
<213> ORGANISM: Rattus norvegicus
<220> FEATURE:
<221> NAME/KEY: misc_feature
<222> LOCATION: (8)..(8)
<223> OTHER INFORMATION: n can be any nucleotide

<400> SEQUENCE: 173
ugcgcuunac aaauc                                                      15

<210> SEQ ID NO 174
<211> LENGTH: 17
<212> TYPE: RNA
<213> ORGANISM: Rattus norvegicus
<220> FEATURE:
<221> NAME/KEY: misc_feature
<222> LOCATION: (9)..(9)
```

<223> OTHER INFORMATION: n can be any nucleotide

<400> SEQUENCE: 174
augcgcuuna caaaucu                                           17

<210> SEQ ID NO 175
<211> LENGTH: 19
<212> TYPE: RNA
<213> ORGANISM: Rattus norvegicus
<220> FEATURE:
<221> NAME/KEY: misc_feature
<222> LOCATION: (10)..(10)
<223> OTHER INFORMATION: n can be any nucleotide

<400> SEQUENCE: 175
gaugcgcuun acaaaucug                                         19

<210> SEQ ID NO 176
<211> LENGTH: 9
<212> TYPE: DNA
<213> ORGANISM: Rattus norvegicus

<400> SEQUENCE: 176 cttgacgaa                                                     9

<210> SEQ ID NO 177
<211> LENGTH: 15
<212> TYPE: DNA
<213> ORGANISM: Rattus norvegicus

<400> SEQUENCE: 177
cgcttgacga atctg                                             15

<210> SEQ ID NO 178
<211> LENGTH: 15
<212> TYPE: DNA
<213> ORGANISM: Rattus norvegicus

<400> SEQUENCE: 178
gcgcttgacg aatct                                             15

<210> SEQ ID NO 179
<211> LENGTH: 15
<212> TYPE: DNA
<213> ORGANISM: Rattus norvegicus

<400> SEQUENCE: 179
tgcgcttgac gaatc                                             15

<210> SEQ ID NO 180
<211> LENGTH: 15
<212> TYPE: DNA
<213> ORGANISM: Rattus norvegicus

<400> SEQUENCE: 180
atgcgcttga cgaat                                             15

<210> SEQ ID NO 181
<211> LENGTH: 16
<212> TYPE: DNA
<213> ORGANISM: Rattus norvegicus

<400> SEQUENCE: 181
gcgcttgacg aatctg                                            16

<210> SEQ ID NO 182
<211> LENGTH: 16
<212> TYPE: DNA
<213> ORGANISM: Rattus norvegicus

<400> SEQUENCE: 182
tgcgcttgac gaatct                                              16

<210> SEQ ID NO 183
<211> LENGTH: 16
<212> TYPE: DNA
<213> ORGANISM: Rattus norvegicus

<400> SEQUENCE: 183
atgcgcttga cgaatc                                              16

<210> SEQ ID NO 184
<211> LENGTH: 17
<212> TYPE: DNA
<213> ORGANISM: Rattus norvegicus

<400> SEQUENCE: 184
tgcgcttgac gaatctg                                             17

<210> SEQ ID NO 185
<211> LENGTH: 17
<212> TYPE: DNA
<213> ORGANISM: Rattus norvegicus

<400> SEQUENCE: 185
atgcgcttga cgaatct                                             17

<210> SEQ ID NO 186
<211> LENGTH: 18
<212> TYPE: DNA
<213> ORGANISM: Rattus norvegicus

<400> SEQUENCE: 186
atgcgcttga cgaatctg                                            18

<210> SEQ ID NO 187
<211> LENGTH: 15
<212> TYPE: DNA
<213> ORGANISM: Rattus norvegicus
<220> FEATURE:
<221> NAME/KEY: misc_feature
<222> LOCATION: (8)..(8)
<223> OTHER INFORMATION: n can be any nucleotide

<400> SEQUENCE: 187
cgcttganga atctg                                               15

<210> SEQ ID NO 188
<211> LENGTH: 17
<212> TYPE: DNA
<213> ORGANISM: Rattus norvegicus
<220> FEATURE:
<221> NAME/KEY: misc_feature
<222> LOCATION: (9)..(9)
<223> OTHER INFORMATION: n can be any nucleotide
<220> FEATURE:
<221> NAME/KEY: misc_feature
<222> LOCATION: (17)..(17)
<223> OTHER INFORMATION: n can be any nucleotide

```
<400> SEQUENCE: 188
gcgcttgang aatctgn                                                    17

<210> SEQ ID NO 189
<211> LENGTH: 19
<212> TYPE: DNA
<213> ORGANISM: Rattus norvegicus
<220> FEATURE:
<221> NAME/KEY: misc_feature
<222> LOCATION: (10)..(10)
<223> OTHER INFORMATION: n can be any nucleotide
<220> FEATURE:
<221> NAME/KEY: misc_feature
<222> LOCATION: (18)..(18)
<223> OTHER INFORMATION: n can be any nucleotide
<220> FEATURE:
<221> NAME/KEY: misc_feature
<222> LOCATION: (19)..(19)
<223> OTHER INFORMATION: n can be any nucleotide

<400> SEQUENCE: 189
tgcgcttgan gaatctgnn                                                  19

<210> SEQ ID NO 190
<211> LENGTH: 15
<212> TYPE: RNA
<213> ORGANISM: Rattus norvegicus
<220> FEATURE:
<221> NAME/KEY: misc_feature
<222> LOCATION: (8)..(8)
<223> OTHER INFORMATION: n can be any nucleotide

<400> SEQUENCE: 190
ugcgcuunac gaauc                                                      15

<210> SEQ ID NO 191
<211> LENGTH: 17
<212> TYPE: RNA
<213> ORGANISM: Rattus norvegicus
<220> FEATURE:
<221> NAME/KEY: misc_feature
<222> LOCATION: (9)..(9)
<223> OTHER INFORMATION: n can be any nucleotide

<400> SEQUENCE: 191
augcgcuuna cgaaucu                                                    17

<210> SEQ ID NO 192
<211> LENGTH: 19
<212> TYPE: RNA
<213> ORGANISM: Rattus norvegicus
<220> FEATURE:
<221> NAME/KEY: misc_feature
<222> LOCATION: (1)..(1)
<223> OTHER INFORMATION: n can be any nucleotide
<220> FEATURE:
<221> NAME/KEY: misc_feature
<222> LOCATION: (10)..(10)
<223> OTHER INFORMATION: n can be any nucleotide

<400> SEQUENCE: 192
naugcgcuun acgaaucug                                                  19

<210> SEQ ID NO 193
<211> LENGTH: 9
<212> TYPE: DNA
<213> ORGANISM: Rattus norvegicus

<400> SEQUENCE: 193
``` ccagacatg 9

<210> SEQ ID NO 194
<211> LENGTH: 15
<212> TYPE: DNA
<213> ORGANISM: Rattus norvegicus

<400> SEQUENCE: 194
ctccagacat gtgga 15

<210> SEQ ID NO 195
<211> LENGTH: 15
<212> TYPE: DNA
<213> ORGANISM: Rattus norvegicus

<400> SEQUENCE: 195
gctccagaca tgtgg 15

<210> SEQ ID NO 196
<211> LENGTH: 15
<212> TYPE: DNA
<213> ORGANISM: Rattus norvegicus

<400> SEQUENCE: 196
agctccagac atgtg 15

<210> SEQ ID NO 197
<211> LENGTH: 15
<212> TYPE: DNA
<213> ORGANISM: Rattus norvegicus

<400> SEQUENCE: 197
cagctccaga catgt 15

<210> SEQ ID NO 198
<211> LENGTH: 16
<212> TYPE: DNA
<213> ORGANISM: Rattus norvegicus

<400> SEQUENCE: 198
gctccagaca tgtgga 16

<210> SEQ ID NO 199
<211> LENGTH: 16
<212> TYPE: DNA
<213> ORGANISM: Rattus norvegicus

<400> SEQUENCE: 199
agctccagac atgtgg 16

<210> SEQ ID NO 200
<211> LENGTH: 16
<212> TYPE: DNA
<213> ORGANISM: Rattus norvegicus

<400> SEQUENCE: 200
cagctccaga catgtg 16

<210> SEQ ID NO 201
<211> LENGTH: 17
<212> TYPE: DNA
<213> ORGANISM: Rattus norvegicus

<400> SEQUENCE: 201
agctccagac atgtgga                                                        17

<210> SEQ ID NO 202
<211> LENGTH: 17
<212> TYPE: DNA
<213> ORGANISM: Rattus norvegicus

<400> SEQUENCE: 202
cagctccaga catgtgg                                                        17

<210> SEQ ID NO 203
<211> LENGTH: 18
<212> TYPE: DNA
<213> ORGANISM: Rattus norvegicus

<400> SEQUENCE: 203
cagctccaga catgtgga                                                       18

<210> SEQ ID NO 204
<211> LENGTH: 15
<212> TYPE: DNA
<213> ORGANISM: Rattus norvegicus
<220> FEATURE:
<221> NAME/KEY: misc_feature
<222> LOCATION: (8)..(8)
<223> OTHER INFORMATION: n can be any nucleotide

<400> SEQUENCE: 204
ctccaganat gtgga                                                          15

<210> SEQ ID NO 205
<211> LENGTH: 17
<212> TYPE: DNA
<213> ORGANISM: Rattus norvegicus
<220> FEATURE:
<221> NAME/KEY: misc_feature
<222> LOCATION: (9)..(9)
<223> OTHER INFORMATION: n can be any nucleotide

<400> SEQUENCE: 205
gctccagana tgtggaa                                                        17

<210> SEQ ID NO 206
<211> LENGTH: 19
<212> TYPE: DNA
<213> ORGANISM: Rattus norvegicus
<220> FEATURE:
<221> NAME/KEY: misc_feature
<222> LOCATION: (10)..(10)
<223> OTHER INFORMATION: n can be any nucleotide

<400> SEQUENCE: 206
agctccagan atgtggaat                                                      19

<210> SEQ ID NO 207
<211> LENGTH: 15
<212> TYPE: RNA
<213> ORGANISM: Rattus norvegicus
<220> FEATURE:
<221> NAME/KEY: misc_feature
<222> LOCATION: (8)..(8)
<223> OTHER INFORMATION: n can be any nucleotide

<400> SEQUENCE: 207
agcuccanac augug                                                          15

```
<210> SEQ ID NO 208
<211> LENGTH: 17
<212> TYPE: RNA
<213> ORGANISM: Rattus norvegicus
<220> FEATURE:
<221> NAME/KEY: misc_feature
<222> LOCATION: (9)..(9)
<223> OTHER INFORMATION: n can be any nucleotide

<400> SEQUENCE: 208
cagcuccana caugugg                                                        17

<210> SEQ ID NO 209
<211> LENGTH: 19
<212> TYPE: RNA
<213> ORGANISM: Rattus norvegicus
<220> FEATURE:
<221> NAME/KEY: misc_feature
<222> LOCATION: (1)..(1)
<223> OTHER INFORMATION: n can be any nucleotide
<220> FEATURE:
<221> NAME/KEY: misc_feature
<222> LOCATION: (10)..(10)
<223> OTHER INFORMATION: n can be any nucleotide

<400> SEQUENCE: 209
ncagcuccan acaugugga                                                      19

<210> SEQ ID NO 210
<211> LENGTH: 9
<212> TYPE: DNA
<213> ORGANISM: Rattus norvegicus

<400> SEQUENCE: 210 ccaggcagg                                                                  9

<210> SEQ ID NO 211
<211> LENGTH: 15
<212> TYPE: DNA
<213> ORGANISM: Rattus norvegicus

<400> SEQUENCE: 211
ctccaggcag gtgga                                                          15

<210> SEQ ID NO 212
<211> LENGTH: 15
<212> TYPE: DNA
<213> ORGANISM: Rattus norvegicus

<400> SEQUENCE: 212
gctccaggca ggtgg                                                          15

<210> SEQ ID NO 213
<211> LENGTH: 15
<212> TYPE: DNA
<213> ORGANISM: Rattus norvegicus

<400> SEQUENCE: 213
agctccaggc aggtg                                                          15

<210> SEQ ID NO 214
<211> LENGTH: 15
<212> TYPE: DNA
<213> ORGANISM: Rattus norvegicus
```

```
<400> SEQUENCE: 214
cagctccagg caggt                                                15

<210> SEQ ID NO 215
<211> LENGTH: 16
<212> TYPE: DNA
<213> ORGANISM: Rattus norvegicus

<400> SEQUENCE: 215
gctccaggca ggtgga                                               16

<210> SEQ ID NO 216
<211> LENGTH: 16
<212> TYPE: DNA
<213> ORGANISM: Rattus norvegicus

<400> SEQUENCE: 216
agctccaggc aggtgg                                               16

<210> SEQ ID NO 217
<211> LENGTH: 16
<212> TYPE: DNA
<213> ORGANISM: Rattus norvegicus

<400> SEQUENCE: 217
cagctccagg caggtg                                               16

<210> SEQ ID NO 218
<211> LENGTH: 17
<212> TYPE: DNA
<213> ORGANISM: Rattus norvegicus

<400> SEQUENCE: 218
agctccaggc aggtgga                                              17

<210> SEQ ID NO 219
<211> LENGTH: 17
<212> TYPE: DNA
<213> ORGANISM: Rattus norvegicus

<400> SEQUENCE: 219
cagctccagg caggtgg                                              17

<210> SEQ ID NO 220
<211> LENGTH: 18
<212> TYPE: DNA
<213> ORGANISM: Rattus norvegicus

<400> SEQUENCE: 220
cagctccagg caggtgga                                             18

<210> SEQ ID NO 221
<211> LENGTH: 9
<212> TYPE: DNA
<213> ORGANISM: Rattus norvegicus

<400> SEQUENCE: 221 tacgactcc                                                        9

<210> SEQ ID NO 222
<211> LENGTH: 15
<212> TYPE: DNA
<213> ORGANISM: Rattus norvegicus
```

```
<400> SEQUENCE: 222
ggtacgactc ctggt                                                    15

<210> SEQ ID NO 223
<211> LENGTH: 15
<212> TYPE: DNA
<213> ORGANISM: Rattus norvegicus

<400> SEQUENCE: 223
gggtacgact cctgg                                                    15

<210> SEQ ID NO 224
<211> LENGTH: 15
<212> TYPE: DNA
<213> ORGANISM: Rattus norvegicus

<400> SEQUENCE: 224
cgggtacgac tcctg                                                    15

<210> SEQ ID NO 225
<211> LENGTH: 15
<212> TYPE: DNA
<213> ORGANISM: Rattus norvegicus

<400> SEQUENCE: 225
ccgggtacga ctcct                                                    15

<210> SEQ ID NO 226
<211> LENGTH: 16
<212> TYPE: DNA
<213> ORGANISM: Rattus norvegicus

<400> SEQUENCE: 226
gggtacgact cctggt                                                   16

<210> SEQ ID NO 227
<211> LENGTH: 16
<212> TYPE: DNA
<213> ORGANISM: Rattus norvegicus

<400> SEQUENCE: 227
cgggtacgac tcctgg                                                   16

<210> SEQ ID NO 228
<211> LENGTH: 16
<212> TYPE: DNA
<213> ORGANISM: Rattus norvegicus

<400> SEQUENCE: 228
ccgggtacga ctcctg                                                   16

<210> SEQ ID NO 229
<211> LENGTH: 17
<212> TYPE: DNA
<213> ORGANISM: Rattus norvegicus

<400> SEQUENCE: 229
cgggtacgac tcctggt                                                  17

<210> SEQ ID NO 230
<211> LENGTH: 17
<212> TYPE: DNA
```

<213> ORGANISM: Rattus norvegicus

<400> SEQUENCE: 230
ccgggtacga ctcctgg                                                17

<210> SEQ ID NO 231
<211> LENGTH: 18
<212> TYPE: DNA
<213> ORGANISM: Rattus norvegicus

<400> SEQUENCE: 231
ccgggtacga ctcctggt                                               18

<210> SEQ ID NO 232
<211> LENGTH: 15
<212> TYPE: DNA
<213> ORGANISM: Rattus norvegicus
<220> FEATURE:
<221> NAME/KEY: misc_feature
<222> LOCATION: (8)..(8)
<223> OTHER INFORMATION: n can be any nucleotide

<400> SEQUENCE: 232
ggtacgantc ctggt                                                  15

<210> SEQ ID NO 233
<211> LENGTH: 17
<212> TYPE: DNA
<213> ORGANISM: Rattus norvegicus
<220> FEATURE:
<221> NAME/KEY: misc_feature
<222> LOCATION: (9)..(9)
<223> OTHER INFORMATION: n can be any nucleotide

<400> SEQUENCE: 233
gggtacgant cctggta                                                17

<210> SEQ ID NO 234
<211> LENGTH: 19
<212> TYPE: DNA
<213> ORGANISM: Rattus norvegicus
<220> FEATURE:
<221> NAME/KEY: misc_feature
<222> LOCATION: (10)..(10)
<223> OTHER INFORMATION: n can be any nucleotide

<400> SEQUENCE: 234
cgggtacgan tcctggtag                                              19

<210> SEQ ID NO 235
<211> LENGTH: 15
<212> TYPE: RNA
<213> ORGANISM: Rattus norvegicus
<220> FEATURE:
<221> NAME/KEY: misc_feature
<222> LOCATION: (8)..(8)
<223> OTHER INFORMATION: n can be any nucleotide

<400> SEQUENCE: 235
cggguacnac uccug                                                  15

<210> SEQ ID NO 236
<211> LENGTH: 17
<212> TYPE: RNA
<213> ORGANISM: Rattus norvegicus
<220> FEATURE:
<221> NAME/KEY: misc_feature

```
<222> LOCATION: (9)..(9)
<223> OTHER INFORMATION: n can be any nucleotide

<400> SEQUENCE: 236
ccggguacna cuccugg                                                17

<210> SEQ ID NO 237
<211> LENGTH: 19
<212> TYPE: RNA
<213> ORGANISM: Rattus norvegicus
<220> FEATURE:
<221> NAME/KEY: misc_feature
<222> LOCATION: (1)..(1)
<223> OTHER INFORMATION: n can be any nucleotide
<220> FEATURE:
<221> NAME/KEY: misc_feature
<222> LOCATION: (10)..(10)
<223> OTHER INFORMATION: n can be any nucleotide

<400> SEQUENCE: 237 nccgguacn acuccuggu                                               19

<210> SEQ ID NO 238
<211> LENGTH: 9
<212> TYPE: DNA
<213> ORGANISM: Rattus norvegicus

<400> SEQUENCE: 238 tgcggctct                                                          9

<210> SEQ ID NO 239
<211> LENGTH: 15
<212> TYPE: DNA
<213> ORGANISM: Rattus norvegicus

<400> SEQUENCE: 239
ggtgcggctc ttggc                                                  15

<210> SEQ ID NO 240
<211> LENGTH: 15
<212> TYPE: DNA
<213> ORGANISM: Rattus norvegicus

<400> SEQUENCE: 240
gggtgcggct cttgg                                                  15

<210> SEQ ID NO 241
<211> LENGTH: 15
<212> TYPE: DNA
<213> ORGANISM: Rattus norvegicus

<400> SEQUENCE: 241
cgggtgcggc tcttg                                                  15

<210> SEQ ID NO 242
<211> LENGTH: 15
<212> TYPE: DNA
<213> ORGANISM: Rattus norvegicus

<400> SEQUENCE: 242
ccgggtgcgg ctctt                                                  15

<210> SEQ ID NO 243
<211> LENGTH: 16
<212> TYPE: DNA
```

```
<213> ORGANISM: Rattus norvegicus

<400> SEQUENCE: 243
gggtgcggct cttggc                                               16

<210> SEQ ID NO 244
<211> LENGTH: 16
<212> TYPE: DNA
<213> ORGANISM: Rattus norvegicus

<400> SEQUENCE: 244
cgggtgcggc tcttgg                                               16

<210> SEQ ID NO 245
<211> LENGTH: 16
<212> TYPE: DNA
<213> ORGANISM: Rattus norvegicus

<400> SEQUENCE: 245
ccgggtgcgg ctcttg                                               16

<210> SEQ ID NO 246
<211> LENGTH: 17
<212> TYPE: DNA
<213> ORGANISM: Rattus norvegicus

<400> SEQUENCE: 246
cgggtgcggc tcttggc                                              17

<210> SEQ ID NO 247
<211> LENGTH: 17
<212> TYPE: DNA
<213> ORGANISM: Rattus norvegicus

<400> SEQUENCE: 247
ccgggtgcgg ctcttgg                                              17

<210> SEQ ID NO 248
<211> LENGTH: 18
<212> TYPE: DNA
<213> ORGANISM: Rattus norvegicus

<400> SEQUENCE: 248
ccgggtgcgg ctcttggc                                             18

<210> SEQ ID NO 249
<211> LENGTH: 33
<212> TYPE: DNA
<213> ORGANISM: Rattus norvegicus

<400> SEQUENCE: 249
atgtcatgag gctagctaca acgaggttag ggg                            33

<210> SEQ ID NO 250
<211> LENGTH: 18
<212> TYPE: DNA
<213> ORGANISM: artificial sequence
<220> FEATURE:
<223> OTHER INFORMATION: synthetic sequence

<400> SEQUENCE: 250
catgctatga gcgttgag                                             18
```

-continued

```
<210> SEQ ID NO 251
<211> LENGTH: 18
<212> TYPE: DNA
<213> ORGANISM: artificial sequence
<220> FEATURE:
<223> OTHER INFORMATION: synthetic sequence

<400> SEQUENCE: 251
atctgtttga gcgtctac                                                    18
```